(12) United States Patent
Gellerfors et al.

(10) Patent No.: US 8,106,164 B2
(45) Date of Patent: Jan. 31, 2012

(54) ANTIBODIES SPECIFIC FOR SOLUBLE AMYLOID BETA PEPTIDE PROTOFIBRILS AND USES THEREOF

(75) Inventors: Pär Gellerfors, Lidingo (SE); Lars Lannfelt, Stockholm (SE)

(73) Assignee: BioArctic Neuroscience AB, Stockholm (SE)

( * ) Notice: Subject to any disclaimer, the term of this patent is extended or adjusted under 35 U.S.C. 154(b) by 614 days.

(21) Appl. No.: 11/570,995

(22) PCT Filed: Jun. 21, 2005

(86) PCT No.: PCT/SE2005/000993
§ 371 (c)(1),
(2), (4) Date: Dec. 20, 2006

(87) PCT Pub. No.: WO2005/123775
PCT Pub. Date: Dec. 29, 2005

(65) Prior Publication Data
US 2009/0155246 A1      Jun. 18, 2009

(30) Foreign Application Priority Data
Jun. 21, 2004 (SE) ...................................... 0401601

(51) Int. Cl.
C07K 16/00 (2006.01)
A61K 39/35 (2006.01)

(52) U.S. Cl. ............. 530/388.24; 424/141.1; 424/158.1; 530/388.1; 530/387.1; 530/387.8; 530/387.9

(58) Field of Classification Search .................. None
See application file for complete search history.

(56) References Cited

U.S. PATENT DOCUMENTS

| | | | |
|---|---|---|---|
| 5,604,102 A | 2/1997 | McConlogue et al. |
| 5,612,486 A | 3/1997 | McConlogue et al. |
| 5,679,531 A | 10/1997 | König et al. |
| 5,753,624 A | 5/1998 | McMichael et al. |
| 5,817,626 A | 10/1998 | Findeis et al. |
| 5,850,003 A | 12/1998 | McLonlogue et al. |
| 5,851,996 A | 12/1998 | Kline |
| 5,854,204 A | 12/1998 | Findeis et al. |
| 5,854,215 A | 12/1998 | Findeis et al. |
| 5,985,242 A | 11/1999 | Findeis et al. |
| 6,054,114 A | 4/2000 | Lansbury, Jr. et al. |
| 6,114,133 A | 9/2000 | Seubert et al. |
| 6,174,916 B1 | 1/2001 | McMichael |
| 6,218,506 B1 | 4/2001 | Krafft et al. |
| 6,245,964 B1 | 6/2001 | McLonlogue et al. |
| 6,303,567 B1 | 10/2001 | Findeis et al. |
| 6,319,498 B1 | 11/2001 | Findeis et al. |
| 7,179,463 B2 | 2/2007 | Lannfelt et al. |
| 7,427,392 B1 | 9/2008 | Seubert et al. |
| 2002/0162129 A1 | 10/2002 | Lannfelt et al. |
| 2003/0068316 A1 | 4/2003 | Klein et al. |
| 2003/0187011 A1 | 10/2003 | Lashuel et al. |
| 2003/0232758 A1 | 12/2003 | St. George-Hyslop et al. |
| 2004/0049134 A1 | 3/2004 | Tosaya et al. |
| 2004/0170641 A1 | 9/2004 | Schenk |
| 2004/0171815 A1 | 9/2004 | Schenk et al. |
| 2004/0171816 A1 | 9/2004 | Schenk et al. |
| 2005/0031629 A1 | 2/2005 | Schenk |
| 2005/0124016 A1 | 6/2005 | LaDu et al. |
| 2005/0142132 A1 | 6/2005 | Schenk et al. |
| 2005/0191314 A1 | 9/2005 | Schenk |
| 2005/0249725 A1 | 11/2005 | Schenk et al. |
| 2006/0079447 A1 | 4/2006 | Wetzel |
| 2006/0166275 A1 | 7/2006 | Krafft et al. |
| 2006/0178302 A1 | 8/2006 | Krafft et al. |
| 2006/0193850 A1 | 8/2006 | Warne et al. |
| 2006/0228349 A1 | 10/2006 | Acton et al. |
| 2006/0240486 A1 | 10/2006 | Johnson-Wood et al. |
| 2006/0280733 A1 | 12/2006 | Kayed et al. |
| 2007/0048312 A1 | 3/2007 | Klein et al. |
| 2007/0081998 A1 | 4/2007 | Kinney et al. |
| 2007/0098721 A1 | 5/2007 | Hillen et al. |
| 2007/0099185 A1 | 5/2007 | Hagen et al. |
| 2007/0110750 A1 | 5/2007 | Glabe et al. |
| 2007/0148167 A1 | 6/2007 | Strohl |
| 2008/0181902 A1 | 7/2008 | Lannfelt et al. |

FOREIGN PATENT DOCUMENTS

| | | |
|---|---|---|
| EP | 0 783 104 | 7/1997 |
| WO | WO 91/16819 | 11/1991 |
| WO | WO 95/11994 | 5/1995 |
| WO | WO 95/31996 | 11/1995 |
| WO | WO 96/15452 A1 | 5/1996 |
| WO | WO 97/41856 | 11/1997 |
| WO | WO 98/33815 | 8/1998 |
| WO | WO 99/27944 | 6/1999 |

(Continued)

OTHER PUBLICATIONS

Klein et al., "Oligemia-Induced Expression of c-fos and Oxidative Stress-Related Protein in the Murine Brain," 30th Annual Meeting of the Society of Neuroscience, New Orleans, LA, Nov. 4-9, 2000, *Soc. Neurosci. Abstracts* 26(1-2), Abstract 383.15, 2000.

Klyubin et al., "Inhibitory Effect of Amyloid-β Peptide with the Arctic Mutation on Long-term Potentiation in Area CA1 of Rat Hippocampus In Vivo," *J. Physiol.* 551P, C32, 2003.

Nichols et al., "Growth of β-amyloid(1-40) Protofibrils by Monomer Elongation and Lateral Association. Characterization of Distinct Products by Light Scattering and Atomic Force Microscopy," *Biochemistry* 41(19):6115-6127, 2002.

(Continued)

*Primary Examiner* — Olga N Chernyshev
(74) *Attorney, Agent, or Firm* — Clark & Elbing LLP

(57) ABSTRACT

The invention pertains to the development of antibodies that specifically bind amyloid beta protein (Abeta) in its protofibril conformation. The invention also comprises methods of using anti-Abeta protofibril antibodies to diagnose or treat Alzheimer's disease, Down's syndrome Lewybody dementia, vascular dementia, and other neurodegenerative disorders. Furthermore, the invention pertains to the use of anti-Abeta protofibril antibodies to screen and identify substances that will modulate protofibril activity or formation in vitro or in vivo. The invention also pertains to methods for synthesising pure Abeta protofibril antigens as well as to a method for stabilising Abeta protofibrils antigens as well as to a method for stabilising Abeta protofibrils.

9 Claims, 8 Drawing Sheets

FOREIGN PATENT DOCUMENTS

Figure 1:
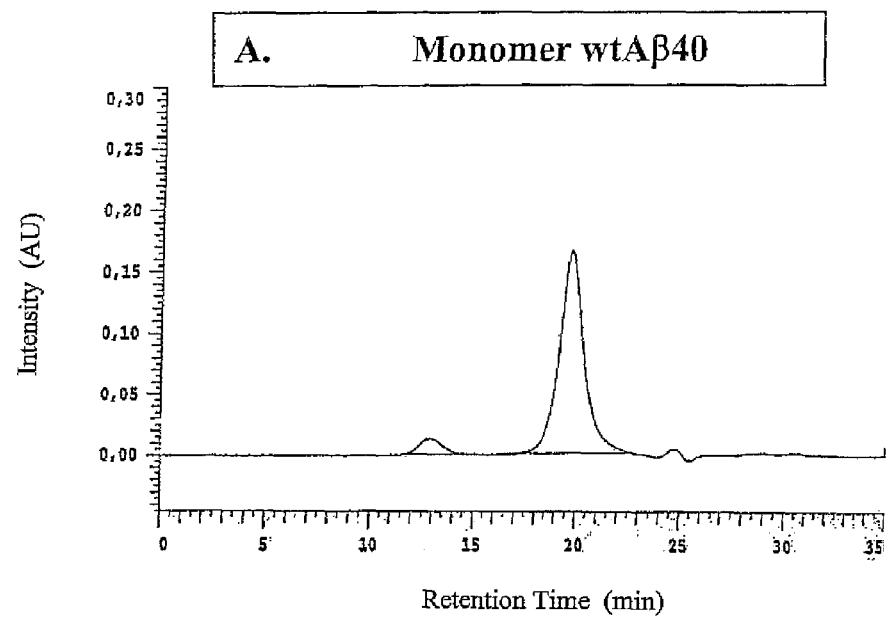
Figure 1:
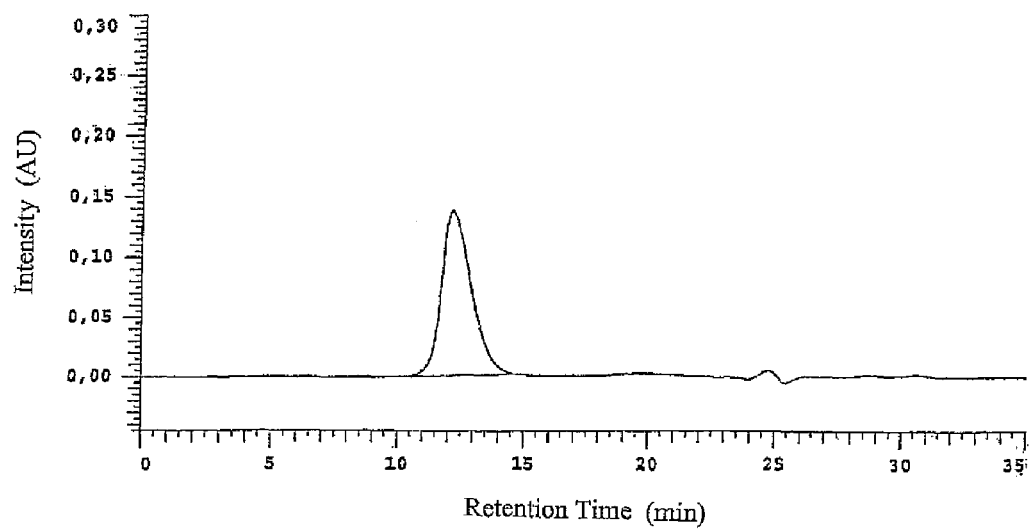
Figure 1:
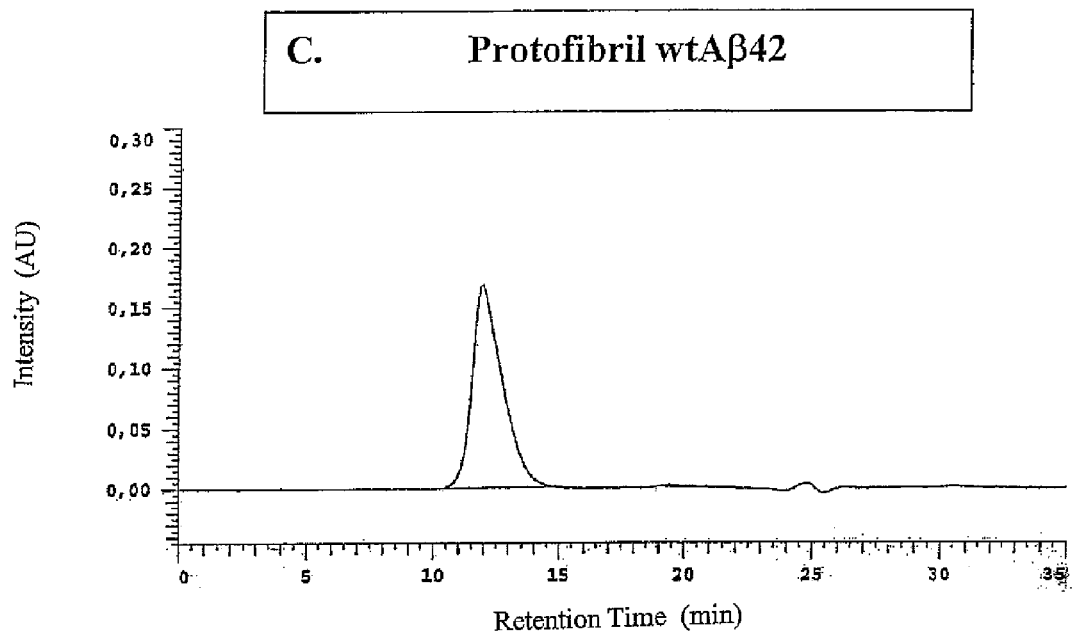
Figure 1:
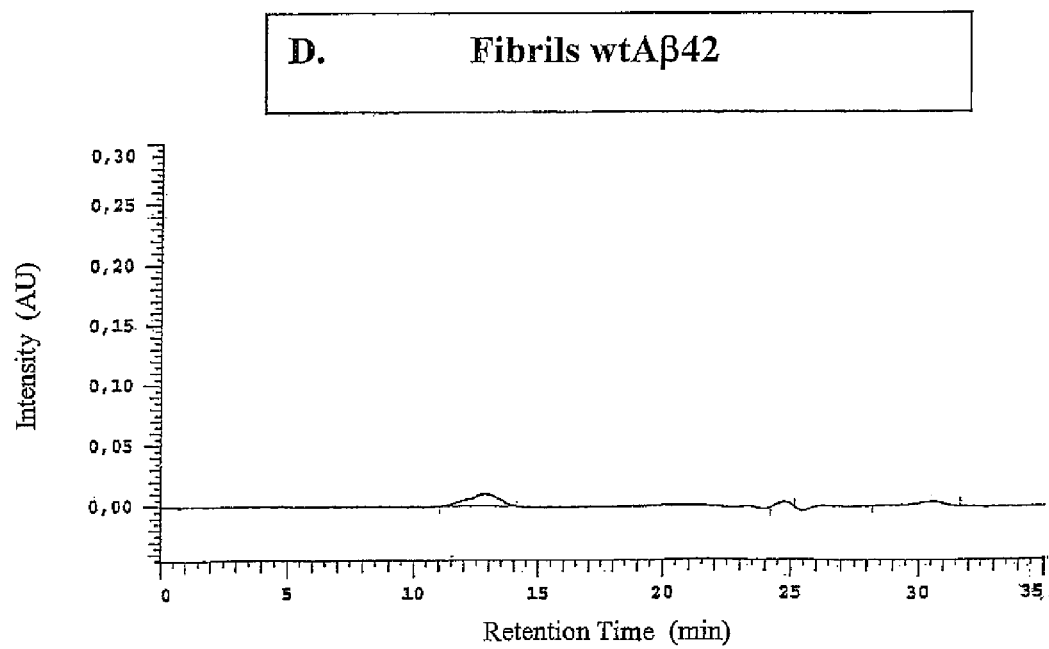

| WO | WO 99/27944 A1 | 6/1999 |
|---|---|---|
| WO | WO 99/27949 | 6/1999 |
| WO | WO 00/39310 | 7/2000 |
| WO | WO 00/71671 | 11/2000 |
| WO | WO 00/72870 | 12/2000 |
| WO | WO 00/72876 | 12/2000 |
| WO | WO 00/72880 | 12/2000 |
| WO | WO 01/10900 | 2/2001 |
| WO | WO 01/39796 | 6/2001 |
| WO | WO 01/90182 | 11/2001 |
| WO | 02/03911 | 1/2002 |
| WO | WO 02/03911 A2 | 1/2002 |
| WO | 03/089460 | 10/2003 |
| WO | WO 03/089460 | 10/2003 |
| WO | WO 03/104437 | 12/2003 |
| WO | WO 2004/024090 | 3/2004 |
| WO | WO 2004/031400 | 4/2004 |
| WO | 2005/025516 A2 | 3/2005 |
| WO | WO 2005/019828 | 3/2005 |
| WO | WO 2005/025516 | 3/2005 |
| WO | 2005/089539 | 9/2005 |
| WO | WO 2005/089539 A1 | 9/2005 |
| WO | WO2005/123775 | 12/2005 |
| WO | WO 2005/123775 A1 | 12/2005 |
| WO | WO 2006/014478 | 2/2006 |
| WO | WO 2006/047254 | 5/2006 |
| WO | WO 2006/055178 | 5/2006 |
| WO | WO 2006/066233 | 6/2006 |
| WO | WO 2006/083533 | 8/2006 |
| WO | WO 2006/094724 | 9/2006 |
| WO | WO 2006/137354 | 12/2006 |
| WO | WO 2007/005358 | 1/2007 |
| WO | WO 2007/005359 | 1/2007 |
| WO | WO 2007/050359 | 5/2007 |
| WO | WO 2007/062088 | 5/2007 |
| WO | WO2007/108756 | 9/2007 |
| WO | WO 2007/108756 A1 | 9/2007 |

OTHER PUBLICATIONS

Tagliavani et al., "A New βAPP Mutation Related to Hereditary Cerebral Haemorrhage," *Alz. Report* 2(Suppl. 1):S28, Abstract 23, 1999.
Communication from European Patent Application No. 05753672.4-2402, mailed Jul. 6, 2009.
Restriction Requirement (U.S. Appl. No. 09/899,815; U.S. Patent No. 7,179,463), mailed Jul. 3, 2002.
Reply to Restriction Requirement (U.S. Appl. No. 09/899,815; U.S. Patent No. 7,179,463), filed Sep. 3, 2002.
Office Action (U.S. Appl. No. 09/899,815; U.S. Patent No. 7,179,463), mailed Nov. 19, 2002.
Reply to Office Action (U.S. Appl. No. 09/899,815; U.S. Patent No. 7,179,463), filed Apr. 21, 2003.
Office Action (U.S. Appl. No. 09/899,815; U.S. Patent No. 7,179,463), mailed Jun. 25, 2003.
Interview Summary (U.S. Appl. No. 09/899,815; U.S. Patent No. 7,179,463), dated Oct. 21, 2003.
Notice of Appeal (U.S. Appl. No. 09/899,815; U.S. Patent No. 7,179,463), filed Nov. 25, 2003.
Reply to Office Action (U.S. Appl. No. 09/899,815; U.S. Patent No. 7,179,463), filed Dec. 18, 2003.
Resubmission of Reply to Office Action (U.S. Appl. No. 09/899,815; U.S. Patent No. 7,179,463), filed Feb. 3, 2004.
Advisory Action (U.S. Appl. No. 09/899,815; U.S. Patent No. 7,179,463), mailed Feb. 20, 2004.
Request for Continued Examination (U.S. Appl. No. 09/899,815; U.S. Patent No. 7,179,463), filed Mar. 25, 2004.
Restriction Requirement (U.S. Appl. No. 09/899,815; U.S. Patent No. 7,179,463), mailed Jun. 10, 2004.
Reply to Restriction Requirement (U.S. Appl. No. 09/899,815; U.S. Patent No. 7,179,463), filed Sep. 10, 2004.
Supplemental Reply to Restriction Requirement (U.S. Appl. No. 09/899,815; U.S. Patent No. 7,179,463), filed Sep. 21, 2004.
Office Action (U.S. Appl. No. 09/899,815; U.S. Patent No. 7,179,463), mailed Nov. 24, 2004.
Reply to Office Action (U.S. Appl. No. 09/899,815; U.S. Patent No. 7,179,463), filed Mar. 24, 2005.
Office Action (U.S. Appl. No. 09/899,815; U.S. Patent No. 7,179,463), mailed Jul. 7, 2005.
Reply to Office Action (U.S. Appl. No. 09/899,815; U.S. Patent No. 7,179,463), filed Oct. 7, 2005.
Office Action (U.S. Appl. No. 09/899,815; U.S. Patent No. 7,179,463), mailed Nov. 9, 2005.
Reply to Office Action (U.S. Appl. No. 09/899,815; U.S. Patent No. 7,179,463), filed Mar. 9, 2006.
Declaration Under Rule 132 (U.S. Appl. No. 09/899,815; U.S. Patent No. 7,179,463), filed Mar. 9, 2006.
Office Action (U.S. Appl. No. 09/899,815; U.S. Patent No. 7,179,463) mailed May 8, 2006.
Reply to Office Action (U.S. Appl. No. 09/899,815; U.S. Patent No. 7,179,463), filed Aug. 8, 2006.
Notice of Allowance (U.S. Appl. No. 09/899,815; U.S. Patent No. 7,179,463), mailed Oct. 16, 2006.
U.S. Appl. No. 09/369,236, filed Aug. 4, 1999, Krafft et al.
U.S. Appl. No. 09/745,057, filed Dec. 20, 2000, Krafft et al.
U.S. Appl. No. 10/166,856, filed Jun. 11, 2002, Klein et al.
U.S. Appl. No. 60/621,776, filed Oct. 25, 2004, Lambert et al.
U.S. Appl. No. 60/652,538, filed Feb. 14, 2005, Shughrue et al.
U.S. Appl. No. 60/217,098, filed Jul. 10, 2000, Lannfelt et al.
U.S. Appl. No. 11/570,995, filed Dec. 20, 2006, Gellerfors et al.
U.S. Appl. No. 12/294,207, filed Sep. 23, 2008, Gellerfors et al.
Axelman et al., "A Large Swedish Family with Alzheimer's Disease with a Codon 670/671 Amyloid Precursor Protein Mutation," *Arch. Neurol.* 51:1193-1197, 1994.
Forsell et al., "Amyloid Precursor Protein Mutation at Codon 713 (Ala →Val) Does Not Cause Schizophrenia: Non-Pathogenic Variant Found at Codon (Silent)," *Neurosci. Lett.* 184:90-93, 1995.
Jensen et al., "Quantification of Alzheimer Amyloid β Peptides Ending at Residues 40 and 42 by Novel ELISA Systems," *Mol. Med.* 6:291-302, 2000.
Johansson et al., "Physiochemical Characterization of the Alzheimer's Disease-Related Peptides Aβ1-42 Arctic and Aβ1-42 wt" *FEBS J.* 273:2618-2630, 2006.
Johnston et al., "Increased β-Amyloid Release and Levels of Amyloid Precursor Protein (APP) in Fibroblast Cell Lines From Family Members With the Swedish Alzheimer's Disease APP670/671 Mutation," *FEBS Lett.* 354:274-278, 1994.
Lannfelt et al., "Amyloid Precursor Protein Mutation Causes Alzheimer's Disease in a Swedish Family," *Neurosci. Lett.* 168:254-256, 1994.
Lannfelt et al., "Amyloid β-Peptide in Cerebrospinal Fluid in Individuals with the Swedish Alzheimer Amyloid Precursor Protein Mutation," *Neurosci. Lett.* 199:203-206, 1995.
Lannfelt et al., "Genetics of Alzheimer's Disease—Routes to the Pathophysiology," *J. Neural. Transm.* [Suppl.] 59:155-161, 2000.
Lannfelt et al., "Genetics, Pathophysiology and Aβ Protofibril Formation in Alzheimer's Disease," *Neurobiol. Aging* 25(Suppl. 2): Poster Session P2: Epidemiology and Risk Factors of Alzheimer's Disease P2-268; S308, 2004.
Lannfelt et al., "Monoclonal Antibodies Selective for Aβ Protofibrils Reduce Plaque Sensitive Detection of Alzheimer Aβ Protofibrils by Burden in Transgenic Mice Models of Alzheimer's Disease Conformation Specific ELISA," ICAD meeting, Uppsala University, Sweden, Jul. 16, 2006.
Lannfelt et al., "Monoclonal Antibodies Selective for Aβ Protofibrils: Detection of Protofibrils and Reduction of Plaque Burden in Tg-mice Models of Alzheimer's Disease," SfN meeting, Uppsala University, Sweden, Oct. 17, 2006.
Mullan et al., "A Pathogenic Mutation for Probable Alzheimer's Disease in the APP Gene at the N-terminus of β-Amyloid," *Nature Genet.* 1:345-347, 1992.
Nilsberth et al., "A Novel APP Mutation (E693G)—The Arctic Mutation, Causing, Alzheimer's Disease with Vascular Symptoms," *Society for Neuroscience Annual Meeting*, Miami Beach, Abstract, 120.4; Nov. 1999.

Nilsberth et al., "The 'Arctic' APP Mutation (E693G) Causes Alzheimer's Disease by Enhanced Aβ Protofibril Formation," *Neurobiology of Aging*, May-Jun. 2000, 21, Abstract 265, Supplement 1, 1-304.

Nilsberth et al., "The Attic APP Mutation (E693G) Causes Alzheimer's Disease Through a Novel Mechanism: Increased Amyloid β Protofibril Formation and Decreased Amyloid β Levels in Plasma and Conditioned Media," *Neurobiol. Aging* 21:S58, 2000.

Nilsberth et al., "The 'Arctic' APP Mutation (E693G) Causes Alzheimer's Disease by Enhanced Aβ Protofibril Formation," *Nature Neurosci.* 4(9):887-893, 2001.

Päiviö et al., "Unique Physicochemical Profile of β-Amyloid Peptide Variant Aβ1-40E22G Protofibrils: Conceivable Neuropathogen in Arctic Mutant Carriers," *J. Med. Biol.* 339:145-159, 2004.

Sahlin et al., "The Arctic Alzheimer Mutation Favors Intracellular Amyloid-β Production by Making Amyloid Precursor Protein Less Available to α-secretase," *J. Neurochem.* 101:854-862, 2007.

Scheuner et al., "Secreted Amyloid β-Protein Similar to That in the Senile Plaques of Alzheimer's Disease is Increased In Vivo by the Presenilin 1 and 2 and APP Mutations Linked to Familial Alzheimer's Disease," *Nature Med.* 2(8):864-870, 1996.

Stenh et al., "Amyloid-β Oligomers are Inefficiently Measured by Enzyme-Linked Immunosorbent Assay," *Ann. Neurol.* 58: 147-150, 2005.

Stenh et al., "The Arctic Mutation Interferes with Processing of the Amyloid Precursor Protein," *NeuroReport* 13: 1857-1860, 2002.

Minutes from Oral Proceedings for European Patent Application No. 01945896.7-2402, dated Dec. 17, 2008.

European Examination Report (EP 01 945 896.7), dated Apr. 24, 2007.

European Examination Report (EP 01 945 896.7), dated May 22, 2006.

European Examination Report (EP 01 945 896.7), dated Sep. 30, 2005.

Extended European Search Report from European Patent Application No. 07747965.7, dated May 13, 2009.

International Preliminary Report (PCT/US2003/30930), completed Feb. 6, 2006.

International Preliminary Report on Patentability (PCT/US2003/19640), completed Aug. 7, 2006.

International Preliminary Report on Patentability (PCT/SE01/01553), completed Oct. 23, 2002.

International Preliminary Report on Patentability (PCT/SE05/000993), issued Dec. 28, 2006.

International Preliminary Report on Patentability (PCT/SE07/000292), issued Sep. 23, 2008.

International Search Report (PCT/SE01/01553), mailed Feb. 4, 2002.

International Search Report (PCT/SE05/000993), mailed Oct. 4, 2005.

International Search Report (PCT/SE07/000292), mailed Jul. 20, 2007.

Notice of intent to grant a European patent and Annex (Reasons for Decision) (EP 01 945 896.7), dated Mar. 18, 2009.

Reply to Examination Report (European Patent Application No. 01945896.7-2402), mailed Apr. 7, 2006.

Reply to Examination Report (European Patent Application No. 01945896.7-2402), mailed Sep. 22, 2006.

Reply to Examination Report (European Patent Application No. 01945896.7-2402), mailed Nov. 5, 2007.

Request Pursuant to Oral Proceedings (European Patent Application No. 01945896.7-2402), mailed Oct. 10, 2008.

Summons to Attend Oral Proceedings (European Patent Application No. 01945896.7-2402), dated Jul. 25, 2008.

Written Opinion of the International Searching Authority (PCT/SE05/000993), mailed Oct. 4, 2005.

Written Opinion of the International Searching Authority (PCT/SE07/000292), mailed Jul. 20, 2007.

Andreasen and Blennow, "Beta-amyloid (Abeta) Protein in Cerebrospinal Fluid as a Biomarker for Alzheimer's Disease," *Peptides* 23:1205-1214, 2002.

Bacskai et al., "Imaging of Amyloid-β Deposits in Brains of Living Mice Permits Direct Observation of Clearance of Plaques with Immunotherapy," *Nature Med.* 7(3):369-372, 2001.

Bard et al., "Peripherally Administered Antibodies Against Amyloid β-Peptide Enter the Central Nervous System and Reduce Pathology in a Mouse Model of Alzheimer Disease," *Nature Med.* 6(8):916-919, 2000.

Barghorn et al., "Globular Amyloid β-Peptide Oligomer: A Homogenous and Stable Neuropathological Protein in Alzheimer's Disease," *J. Neurochem.* 95:834-47, 2005.

Bayer et al., "Evaluation of the Safety and Immunogenicity of Synthetic Aβ42 (AN1792) in Patients with AD," *Neurology* 64:94-101, 2005.

Bitan et al., "Amyloid β-Protein (Aβ) Assembly: Aβ40 and Aβ42 Oligomerize Through Distinct Pathways," *Proc. Natl. Acad. Sci. U.S.A.* 100:330-5, 2003.

Blanchard et al., "Efficient Reversal of Alzheimer's Disease Fibril Formation and Elimination of Neurotoxicity by a Small Molecule," *Proc. Natl. Acad. Sci. U.S.A.* 101(40):14326-32, 2004.

Cai et al., "Release of Excess Amyloid β-Protein from a Mutant Amyloid β-Protein Precursor," *Science* 259:514-516, 1993.

Caughey and Lansbury, "Protofibrils, Pores, Fibils, and Neurodegeneration: Separating the Responsible Protein Aggregates from the Innocent Bystanders," *Ann. Rev. Neurosci.* 26:267-98, 2003.

Chen et al., "A Learning Deficit Related to Age and β-Amyloid Plaques in a Mouse Model of Alzheimer's Disease," *Nature* 408:975-978, 2000.

Chromy et al., "Self-Assembly of $A\beta_{1-42}$ Into Globular Neurotoxins," *Biochemistry* 42:12749-12760, 2003.

Chromy et al., "Stability of Small Oligomers of $A\beta_{1-42}$(ADDLs)," *Society for Neuroscience* 25:2129; 852.5, 1999.

Citron et al., "Mutation of the β-Amyloid Precursor Protein in Familial Alzheimer's Disease Increases β-Protein Production," *Nature* 360:672-674, 1992.

Citron et al., "Mutant Presenilins of Alzheimer's Disease Increase Production of 42-Residue Amyloid β-Protein in Both Transfected Cells and Transgenic Mice," *Nature Med.* 3(1):67-72, 1997.

Conway et al., "Acceleration of Oligomerization, Not Fibrillization, is a Shared Property of Both α-Synuclein Mutations Linked to Early-Onset Parkinson's Disease: Implications for Pathogenesis and Therapy," *Proc. Natl. Acad. Sci. U.S.A.* 97(2):571-576, 2000.

Dahlgren et al., "Oligomeric and Fibrillar Species of Amyloid-β Peptides Differentially Affect Neuronal Viability," *J. Biol. Chem.* 277:32046-53, 2002.

Dalfo et al., "Evidence of Oxidative Stress in the Neocortex in Incidental Lewy Body Disease," *J. Neuropathol. Exp. Neurol.* 64(9):816-830, 2005.

De Jonghe et al., "Flemish and Dutch Mutations in Amyloid β Precursor Protein Have Different Effects on Amyloid β Secretion," *Neurobiol. Dis.* 5:281-286, 1998.

DeMarco et al., "From Conversion to Aggregation: Protofibril Formation of the Prion Protein," *Proc. Natl. Acad. Sci. U.S.A.* 101:2293-2298, 2004.

Dodart et al., "Immunization Reverses Memory Deficits Without Reducing Brain Aβ Burden in Alzheimer's Disease Model," *Nature Neurosci.* 5:452-457, 2002.

El-Agnaf et al., "Oligomerization and Toxicity of β-Amyloid-42 Implicated in Alzheimer's Disease," *Biochem. Biophys. Res. Comm.* 273:1003-1007, 2000.

Enya et al., "Appearance of Sodium Dodecyl Sulfate-Stable Amyloid β-Protein (Aβ) Dimer in the Cortex During Aging," *Am. J. Pathol.* 154:271-279, 1999.

Finder and Glockshuber, "Amyloid-β Aggregation," *Neurodegener. Dis.* 4(1):13-27, 2007.

Frackowiak et al., "Non-Fibrillar β-Amyloid Protein is Associated with Smooth Muscle Cells of Vessel Walls in Alzheimer Disease," *J. Neuropathol. Exp. Neurol.* 53:637-645, 1994.

Frenkel et al, "Modulation of Alzheimer's Beta-amyloid Neurotoxicity by Site-directed Single-chain Antibody," *Neuroimmunomodulation* 6:444, 1999.

Frenkel et al., "Immunization Against Alzheimer's β-Amyloid Plaques Via EFRH Phage Administration," *Proc. Natl. Acad. Sci. U.S.A.* 97(21):11455-11459, 2000.

Frenkel et al, "Modulation of Alzheimer's Beta-amyloid Neurotoxicity by Site-directed Single-chain Antibody," *J. Neuroimmunol.* 106:23-31, 2000.

Giulian et al., "The HHQK Domain of β-Amyloid Provides a Structural Basis for the Immunopathology of Alzheimer's Disease," *J. Biol. Chem.* 273(45):29719-29726, 1998.

Glenner et al., "Alzheimer's Disease: Initial Report of the Purification and Characterization of a Novel Cerebrovascular Amyloid Protein," *Biochem. Biophys. Res. Comm.* 120(3):885-890, 1984.

Grabowski et al., "Novel Amyloid Precursor Protein Mutation in an Iowa Family with Dementia and Severe Cerebral Amyloid Angiopathy," *Ann. Neurol.* 49:697-705, 2001.

Guerette et al., "Oligomeric Aβ in PBS-Soluble Extracts of Human Alzheimer Brain," *Society for Neuroscience* 25:2129; 852.1, 1999.

Hardy, "Framing β-Amyloid," *Nature Genet.* 1:233-234, 1992.

Hardy, "Amyloid, the Presenilins and Alzheimer's Disease," *Trends Neurosci.* 20(4):154-159, 1997.

Harper et al., "Observation of Metastable Aβ Amyloid Protofibrils by Atomic Force Microscopy," *Chem. Biol.* 4:119-125, 1997.

Hartley et al., "Protofibrillar Intermediates of Amyloid β-Protein Induce Acute Electrophysiological Changes and Progressive Neurotoxicity in Cortical Neurons," *J. Neurosci.* 19(20):8876-8884, 1999.

Hendriks et al., "Presenile Dementia and Cerebral Hemorrhage Linked to a Mutation at Codon 692 of the β-Amyloid Precursor Protein Gene," *Nature Genet.* 1:218-221, 1992.

Hock and Nitsch, "Clinical Observations with AN-1792 Using TAPIR Analyses," *Neurodegener Dis.* 2:273-276, 2005.

Hoshi et al., "Spherical Aggregates of β-Amyloid (Amylospheroid) Show High Neurotoxicity and Activate Tau Protein Kinase I/glycogen Synthase Kinase-3β," *Proc. Natl. Acad. Sci. U.S.A.* 100(11):6370-6375, 2003.

Isaacs et al., "Acceleration of Amyloid β-Peptide Aggregation by Physiological Concentrations of Calcium," *J. Biol. Chem.* 281(38):27916-23, 2006.

Janus et al., "A β Peptide Immunization Reduces Behavioral Impairment and Plaques in a Model of Alzheimer's Disease," *Nature* 408:979-982, 2000.

Kang et al., "The Precursor of Alzheimer's Disease Amyloid A4 Protein Resembles a Cell-surface Receptor," *Nature* 325:733-736, 1987.

Kayed et al., "Immunization With a Molecular Mimic of a Toxic Aggregates Generates a Conformation-Dependent Antibody Specific for High Molecular Weight A Aggregates (Micelles and Protofibrils)," 32nd Annual Meeting of the Society for Neuroscience, Orlando, Florida (*Society for Neuroscience Abstract Viewer and Itinerary Planner*, Abstract No. 685.3, 2002).

Kayed et al., "Common Structure of Soluble Amyloid Oligomers Implies Common Mechanism of Pathogenesis," *Science* 300:486-489, 2003.

Kirkitadze et al., "Paradigm Shifts in Alzheimer's Disease and Other Neurodegenerative Disorders: The Emerging Role of Oligomeric Assemblies," *J. Neurosci. Res.* 1, 69:567-77, 2002.

Klafki et al., "Therapeutic Approaches to Alzheimer's Disease," *Brain* 129:2840-2855, 2006.

Klein et al., "Oligomer/Conformation-Dependent Aβ Antibodies," *Soc. Neurosci. Abstr.* Presentation No. 475.11, Tuesday Nov. 7, 2000.

Klein et al., "Targeting Small Aβ Oligomers: The Solution to an Alzheimer's Disease Conundrum?" *Trends Neurosci.* 24:219-224, 2001.

Klein, "Aβ Toxicity in Alzheimer's Disease," *Contemporary Clinical Neuroscience: Molecular Mechanisms of Neurodegenerative Diseases* 1.1 Introduction, 2001.

Klyubin et al., "Soluble Arctic Amyloid β Protein Inhibits Hippocampal Long-Term Potentiation In Vivo," *Eur. J. Neurosci.* 19:2839-2846, 2004.

Kuo et al., "Water-soluble Aβ (N-40, N-42) Oligomers in Normal and Alzheimer Disease Brains," *J. Biol. Chem.* 271:4077-4081, 1996.

Lambert et al., "Diffusible, Nonfibrillar Ligands Derived From $A\beta_{1-42}$ Are Potent Central Nervous System Neurotoxins," *Proc. Natl. Acad. Sci. U.S.A.* 95:6448-6453, 1998.

Lambert et al., "Neuron Dysfunction and Death Caused by Small Aβ Oligomers: Role of Signal Transduction," *Society for Neuroscience* 25:2129, 1999.

Lambert et al., "Vaccination With Soluble Aβ Oligomers Generates Toxicity-Neutralizing Antibodies," *J. Neurochem.* 79:595-605, 2001.

Lambert et al., "Monoclonal Antibodies that Target Pathological Assemblies of Aβ," *J. Neurochem.* 100:23-35, 2007.

Lashuel et al., "Mixtures of Wild-Type and a Pathogenic (E22G) Form of Aβ40 In Vitro Accumulate Protofibrils, Including Amyloid Pores," *J. Mol. Biol.* 332:795-808, 2003.

Lee et al., "Targeting Amyloid-β Peptide (Aβ) Oligomers by Passive Immunization with a Conformation-selective Monoclonal Antibody Improves Learning and Memory in Aβ Precursor Protein (APP) Transgenic Mice," *J. Biol. Chem.* 2006 281:4292-4299.

Levy et al., "Mutation of the Alzheimer's Disease Amyloid Gene in Hereditary Cerebral Hemorrhage, Dutch Type," *Science* 248:1124-1126, 1990.

Liu et al., "Residues 17-20 and 30-35 of β-Amyloid Play Critical Roles in Aggregation," *J. Neurosci. Res.* 75(2):162-71, 2004.

Longo and Finch, "Nonfibrillar Aβ 1-42 (ADDL) Causes Aconitase Inactivation and Iron-dependent Neurotoxicity," *Society for Neuroscience* 25: 2129, 1999.

Masters et al., "Amyloid Plaque Core Protein in Alzheimer's Disease and Down Syndrome," *Proc. Natl. Acad. Sci. U.S.A.* 82:4245-4249, 1985.

McKhann et al., "Clinical Diagnosis of Alzheimer's Disease: Report of the NINCHS-ADRDA Work Group Under the Auspices of Department of Health and Human Services Task Force on Alzheimer's Disease," *Neurology* 34:939-944, 1994.

Morgan et al., "Aβ Peptide Vaccination Prevents Memory Loss in an Animal Model of Alzheimer's Disease," *Nature* 408:982-985, 2000.

Moss et al., "The Peptide KLVFF-$K_6$ Promotes β-Amyloid(1-40) Protofibril Growth by Association but Does Not Alter Protofibril Effects on Cellular Reduction of 3-(4,5-Dimethylthiazol-2-yl)-2,5-Diphenyltetrazolium Bromide (MTT)," *Mol. Pharmacol.* 64(5):1160-8, 2003.

Motter et al., "Reduction of β-Amyloid Peptide$_{42}$ in the Cerebrospinal Fluid of Patients with Alzheimer's Disease," *Ann. Neurol.* 38:643-648, 1995.

Nichols et al., "Amyloid-β Aggregates Formed at Polar-Nonpolar Interfaces Differ From Amyloid-β Protofibrils Produced in Aqueous Buffers," *Microsc. Res. Tech.* 67(3-4):164-74, 2005.

Nicoll et al., "Neuropathology of Human Alzheimer Disease After Immunization With Amyloid-β Peptide: A Case Report," *Nature Med.* 9(4):448-452, 2003.

Oda et al., "Clusterin (apoJ) Alters the Aggregation of Amyloid β-Peptide (Aβ 1-42) and Forms Slowly Sedimenting Aβ Complexes that Cause Oxidative Stress," *Exp. Neurol.* 136:22-31, 1995.

Oda et al., "Purification and Characterization of Brain Clusterin," *Biochem. Biophys. Res. Comm.* 204:1131-6, 1994.

O'Nuallain et al., "Conformational Abs Recognizes a Generic Amyloid Fibril Epitope," *Proc. Natl. Acad. Sci. U.S.A.* 99:1485-1490, 2002.

Palmert et al., "The β-Amyloid Protein Precursor of Alzheimer Disease Has Soluble Derivatives Found in Human Brain and Cerebrospinal Fluid," *Proc. Natl. Acad. Sci. U.S.A.* 86:6338-6342, 1989.

Pirttilä et al., "Soluble Amyloid β-Protein in the Cerebrospinal Fluid From Patients with Alzheimer's Disease, Vascular Dementia and Controls," *J. Neurol. Sci.* 127:90-95, 1994.

Ponte et al., "A New A4 Amyloid mRNA Contains a Domain Homologous to Serine Proteinase Inhibitors," *Nature* 331:525-527, 1988.

Qin et al., "Effect of 4-Hydroxy-2-Nonenal Modification on Alpha-Synuclein Aggregation," *J. Biol. Chem.* 282(8):5862-5870, 2007.

Roher et al., "Morphology and Toxicity of Aβ-(1-42) Dimer Derived from Neuritic and Vascular Amyloid Deposits of Alzheimer's Disease," *J. Biol. Chem.* 271:20631-20635, 1996.

Russo et al., "Presenilin-1 Mutations in Alzheimer's Disease," *Nature* 405:531-532, 2000.

Rzepecki et al., "Prevention of Alzheimer's Disease-Associated Aβ Aggregation by Rationally Designed Nonpeptitdic β-Sheet Ligands," *J. Biol. Chem.* 279:47497-47505, 2004.

Schenk et al., "Immunization with Amyloid-β Attenuates Alzheimer-Disease-Like Pathology in the PDAPP," *Nature* 400:173-177, 1999.

Selkoe, "Cell Biology of the Amyloid β-Protein Precursor and the Mechanism of Alzheimer's Disease," *Ann. Rev. Cell Biol.* 10:373-403, 1994.

Selkoe, "Normal and Abnormal Biology of the β-Amyloid Precursor Protein," *Ann. Rev. Neurosci.* 17:489-517, 1994.

Serpell, "Alzheimer's Amyloid Fibrils: Structure and Assembly," *Biochim. Biophys. Acta* 1502:16-30, 2000.

Seubert et al., "Isolation and Quantification of Soluble Alzheimer's β-Peptide From Biological Fluids," *Nature* 359:325-327, 1992.

Sherrington et al., "Cloning of a Gene Bearing Missense Mutations in Early-Onset Familial Alzheimer's Disease," *Nature* 375:754-760, 1995.

Shtilerman et al., "Molecular Crowding Accelerates Fibrillization of α-Synuclein: Could an Increase in the Cytoplasmic Protein Concentration Induce Parkinson's Disease?" *Biochemistry* 41:3855-3860, 2002.

Sigurdsson et al., "Immunization With a Nontoxic/Nonfibrillar Amyloid-β Homologous Peptide Reduces Alzheimer's Disease-Associated Pathology in Transgenic Mice," *Am. J. Pathol.* 159(2):439-447, 2001.

Solomon et al., "Disaggregation of Alzheimer β-amyloid by Site-directed mAb," *Proc. Natl. Acad. Sci. U.S.A.* 94:4109-4112, 1997.

Solomon et al., "Monoclonal Antibodies Inhibit In Vitro Fibrillar Aggregation of the Alzheimer Beta-amyloid Peptide," *Proc. Natl. Acad. Sci. U.S.A.* 93:452-455, 1996.

Solomon et al., "Monoclonal Antibodies Restore and Maintain the Soluble Conformation of β-amyloid Peptide," *Neurobiol. Aging*, vol. 17, No. 4, Suppl. 152, 1996.

Soto et al., "The Conformation of Alzheimer's β Peptide Determines the Rate of Amyloid Formation and Its Resistance to Proteolysis," *Biochem. J.* 1:314:701-7, 1996.

Srinivasan et al., "ABri Peptide Associated with Familial British Dementia Forms Annular and Ring-Like Protofibrillar Structures," *Amyloid* 11(1):10-3, 2004.

St. George-Hyslop et al., "The Genetic Defect Causing Familial Alzheimer's Disease Maps on Chromosome 21," *Science* 235:885-890, 1987.

St. George-Hyslop et al., "Genetic Linkage Studies Suggest that Alzheimer's Disease is Not a Single Homogeneous Disorder," *Nature* 347:194-197, 1990.

Stine et al., "The Nanometer-Scale Structure of Amyloid-β Visualized by Atomic Force Microscopy," *J. Prot. Chem.* 15(2):193-203, 1996.

Stine et al., "Supramolecular Structures of Aβ Aggregates and Cellular Responses," Biophysical Journal Program and Abstracts:40th Annual Meeting Feb. 17-21, 1996, *Biophys J.* 70: Abstract 239.

Suzuki et al., "An Increased Percentage of Long Amyloid β Protein Secreted by Familial Amyloid β Protein Precursor (βAPP$_{717}$) Mutants," *Science* 264:1336-1340, 1994.

Vickers, "A Vaccine Against Alzheimer's Disease: Developments to Date," *Drugs Aging* 19(7):487-494, 2002.

Walsh et al., "Amyloid β-Protein Fibrillogenesis. Detection of a Protofibrillar Intermediate," *J. Biol. Chem.* 272:22364-22372, 1997.

Walsh et al., "Amyloid β-Protein Fibrillogenesis. Structure and Biological Activity of Protofibrillar Intermediates," *J. Biol. Chem.* 274(35):25945-25952, 1999.

Walsh et al., "Naturally Secreted Oligomers of Amyloid β Protein Potently Inhibit Hippocampal Long-Term Potentiation In Vivo," *Nature* 416:535-539, 2002.

Walsh et al., "Amyloid-β Oligomers: Their Production, Toxicity and Therapeutic Inhibition," *Biochem. Soc. Trans.* 30:552-7, 2002.

Walsh et al., "Oligomers on the Brain: The Emerging Role of Soluble Protein Aggregates in Neurodegeneration," *Protein Pept. Lett.*, 11: 213-28, 2004.

Ward et al., "Fractionation and Characterization of Oligomeric, Protofibrillar Forms of β-Amyloid Peptide," *Biochem. J.* 348:137-144, 2000.

Weidemann et al., "Identification, Biogenesis, and Localization of Precursors of Alzheimer's Disease A4 Amyloid Protein," *Cell* 57:115-126, 1989.

Weiner et al., "Nasal Administration of Amyloid-β Peptide Decreases Cerebral Amyloid Burden in a Mouse Model of Alzheimer's Disease," *Annals Neurol.* 48(4):567-579, 2000.

Westlind-Danielsson and Arnerup, "Spontaneous In Vitro Formation of Supramolecular β-Amyloid Structures, "βamy Balls", by β-Amyloid 1-40 peptide," *Biochemistry* 40:14736-43, 2001.

Williams et al., "Structural Properties of Aβ Protofibrils Stabilized by a Small Molecule," *Proc. Natl. Acad. Sci. U.S.A.* 102(20):7115-20, 2005.

Wirak et al., "Deposits of Amyloid β Protein in the Central Nervous System of Transgenic Mice," *Science* 253:323-325, 1991.

Ye et al., "Protofibrils of Amyloid β-Protein Inhibit Specific K$^+$ Currents in Neocortical Cultures," *Neurobiol. Dis.* 13:177-190, 2003.

Yoritaka et al., "Immunohistochemical Detection of 4-Hydroxynonenal Protein Adducts in Parkinson Disease," *Proc. Natl. Acad. Sci. U.S.A.* 93:2696-2701, 1996.

Yoshikai et al., "Genomic Organization of the Human Amyloid Beta-protein Precursor Gene," *Gene* 87:257-263, 1990.

Axelman, et al., "A Large Swedish Family with Alzheimer's Disease with a Codon 670/671 Amyloid Precursor Protein Mutation", *Arch. Neurol.*, 51:1193-1197 (1994).

Bard, et al., "Peripherally administered antibodies against amyloid B-peptide enter the central nervous system and reduce pathology in a mouse model of Alzheimer disease", Nature Medicine 6(8):916-919 (Aug. 2000).

Cai, et al., "Release of Excess Amyloid b Protein from a Mutant Amyloid b Protein Precursor", Science, New Series, 259:514-516 (Jan. 22, 1993).

Chromy, et al., "Self-Assembly of Aβ$_{1-42}$ into Globular Neurotoxins", Biochemistry, 42:12749-12760 (2003).

Citron, et al., "Mutation of the β-amyloid precursor protein in familial Alzheimer's disease increases β-protein production", Nature, 360:672-674 (Dec. 17, 1992).

DeMarco, et al., "From conversion to aggregation: Protofibril formation of the prion protein", PNAS., 101:2293-2298 (Feb. 24, 2004).

Dennis J. Selkoe, "Cell Biology of the Amyloid B-Protein Precursor and the Mechanism of Alzheimer's Disease", Annu. Rev. Cell Biol., 10:373-403 (1994).

Dennis J. Selkoe, "Normal and Abnormal Biology of the B-Amyloid Precursor Protein", Annu. Rev. Neurosci., 17:489-517 (1994).

Dodart, et al., "Immunization reverses memory deficits without reducing brain AB burden in alzheimer's disease model", Nature Neuroscience, 5:452-457 (May 2002).

Glenner, et al., "Alzheimer's Disease: Initial Report of the Purification and Characterization of a Novel Cerebrovascular Amyloid Protein", Biochemical and Biophysical Research Communications, 120(3):885-890 (1984).

Harley, et al., "Protofibrillar Intermediates of Amyloid β-Protein Induce Acute Electrophysiological Changes and Progressive Neurotoxicity in Cortical Neurons", The Journal of Neuroscience, 19(20):8876-8884 (Oct. 15, 1999).

Hoshi, et al., "Spherical aggregates of β-amyloid (amylospheroid) show high neurotoxicity and activate tau protein kinase I/glycogen synthase kinase-3β", PNAS, 100(11):6370-6375 (May 27, 2003).

Janus, et al., "Aβ peptide immunization reduces behavioural impairment and plaques in a model of Alzheimer's disease", Nature, 408:979-982 (Dec. 2000).

John Hardy, "Framing β-amyloid", Nature Genetics, 1:233-234 (Jul. 1992).

Johnston, et al., "Increased β-amyloid release and levels of amyloid precursor protein (APP) in fibroblast cell lines from family members with the Swedish Alzheimer's disease APP670/671 mutation", FEBS Letters, 354:274-278 (1994).

Kayed, et al., "Common Structure of Soluble Amyloid Oligomers Implies Common Mechanism of Pathogenesis", Science, 300:486-489 (Apr. 18, 2003).

Klyubin, et al., "Soluble Arctic amyloid β protein inhibits hippocampal long-term potentiation in vivo", European Journal of Neuroscience, 19:2839-2846 (2004).

Lambert, et al., "Diffusible, nonfibrillar ligands derived from Aβ$_{1-42}$ are potent central nervous system neurotoxins", Proc. Natl. Acad. Sci. USA, 95:6448-6453 (May 1998).

Lambert, et al., "Vaccination with soluble Aβ oligomers generates toxicity-neutralizing antibodies", Journal of Neurochemistry, 79:595-605 (2001).

Lannfelt, et al., "Amyloid Precursor Protein Mutation Causes Alzheimer's Disease in a Swedish Family", Neuroscience Letters, 168:254-256 (1994).

Lannfelt, et al., "Amyloid β-peptide in Cerebrospinal Fluid in Individuals with the Swedish Alzheimer Amyloid Precursor Protein Mutation", Neuroscience Letters, 199:203-206 (1995).

Lashuel, et al., "Mixtures of Wild-type and a Pathogenic (E22G) Form of Aβ40 in Vitro Accumulate Protofibrils, Including Amyloid Pores", J. Mol. Biol., 332:795-808 (2003).

Masters, et al., "Amyloid Plaque Core Protein in Alzheimer Disease and Down Syndrome", PNAS, 82:4245-4249 (1985).

McKhann, et al., "Clinical diagnosis of Alzheimer's disease: Report of the NINCDS-ADRDA Work Group* under the auspices of Department of Health and Human Services Task Force on Alzheimer's Disease", Neurology, 34:939-944 (Jul. 1994).

Morgan, et al., "AB peptide vaccination prevents memory loss in an animal model of Alzheimer's disease", Nature, 408:982-985 (Dec. 2000).

Motter, et al., "Reduction of B-Amyloid Peptide$_{42}$ in the Cerebrospinal Fluid of Patients with Alzheimer's Disease", Ann. Neurol., 38:643-648 (1995).

Mullen, et al., "A pathogenic mutation for probable Alzheimer's disease in the APP gene at the N-terminus of β-amyloid", Nature Genetics, 1:345-347 (Aug. 1992).

Nicoll, et al., "Neuropathology of human Alzheimer disease after immunization with amyloid-β peptide: a case report", Nature Medicine, 9:4:448-452 (Apr. 2003).

Nilsberth, et al., "The 'Arctic' APP mutation (E693G) causes Alzheimer's disease by enhanced Aβ protofibril formation", Nature Neuroscience, 4(9):887-893 (2001).

O'Nuallain, et al., "Conformational Abs recognizing a generic amyloid fibril epitope", PNAS., 99:1485-1490 (Feb. 5, 2002).

Pirttilä, et al., "Soluble amyloid β-protein in the cerebrospinal fluid from patients with Alzheimer's disease, vascular dementia and controls", Journal of the Neurological Science, 127:90-95 (1994).

Scheuner, et al., "Secreted amyloid β-protein similar to that in the senile plaques of Alzheimer's disease is increased in vivo by the presenilin 1 and 2 and *APP* mutations linked to familial Alzheimer's disease", Nature Medicine, 2(8):864-870 (Aug. 1996).

Seubert, et al., "Isolation and quantification of soluble Alzheimer's β-peptide from biological fluids", Nature, 359:325-327 (Sep. 1992).

Shtilerman, et al., "Molecular Crowding Accelerates Fibrillization of a-Synuclein: Could an Increase in the Cytoplasmic Protein Concentration Induce Parkinson's Disease?", Biochemistry, 41:3855-3860 (2002).

Sigurdsson, et al., "Immunization with a Nontoxic/Nonfibrillar Amyloid-β Homologous Peptide Reduces Alzheimer's Disease-Associated Pathology in Transgenic Mice", American Journal of Pathology, 159:2:439-447 (Aug. 2001).

Stine, et al., "The Nanometer-Scale Structure of Amyloid-β Visualized by Atomic Force Microscopy", Journal of Protein Chemistry, 15:2:193-203 (1996).

Walsh, et al., "Amyloid β-Protein Fibrillogenesis", The Journal of Biological Chemistry, 274:36:25945-25952 (Sep. 3, 1999).

Walsh, et al., "Naturally secreted oligomers of amyloid β protein potently inhibit hippocampal in vivo", Nature, 416:535-539 (Apr. 4, 2002).

Ward, et al., "Fractionation and characterization of oligomeric, protofibrillar and fibrillar forms of β-amyloid peptide", Biochem. J., 348:137-144 (2000).

Weiner, et al., "Nasal Administration of Amyloid-β Peptide Decreases Cerebral Amyloid Burden in a Mouse Model of Alzheimer's Disease", Annals. of Neurology, 48:4:567-579 (2000).

Ye, et al., "Protofibrils of amyloid β-protein inhibit specific K$^+$ currents in neocortical cultures", Neurobiology of Disease, 13:177-190 (2003).

Giasson et al., "A Panel of Epitope-Specific Antibodies Detects Protein Domains Distributed Throughout Human Alpha-Synuclein in Lewy Bodies of Parkinson's Disease," *J. Neurosci. Res.* 59:528-533, 2000.

Golabek et al., "The Interaction between Apolipoprotein E and Alzheimer's Amyloid β-Peptide Is Dependent on β-Peptide Conformation," *J. Biol. Chem.* 271(18):10602-10606, 1996.

Harper et al., "Assembly of Aβ Amyloid Protofibrils: An In Vitro Model for a Possible Early Event in Alzheimer's Disease," *Biochemistry* 38:8972-8980, 1999.

Kamino et al., "Linkage and Mutational Analysis of Familial Alzheimer Disease Kindreds for the APP Gene Region," *Am. J. Hum. Genet.* 51:998-1014, 1992.

Miravelle et al., "Substitutions at Codon 22 of Alzheimer's Aβ Peptide Induce Diverse Conformational Changes and Apoptotic Effects in Human Cerebral Endothelial Cells," *J. Biol. Chem.* 275:27110-27116, 2000.

Nilsberth et al., "A Novel APP Mutation (E693G)—The Arctic Mutation Causing Alzheimer's Disease with Vascular Symptoms," *Soc. Neurosci. Abstr.* 25:297; 1999.

Schenk et al., "Immunization with Amyloid-β Attenuates Alzheimer-Disease-Like Pathology in the PDAPP Mouse," *Nature* 400:173-177, 1999.

Soto et al., "The Conformation of Alzheimer's β Peptide Determines the Rate of Amyloid Formation and Its Resistance to Proteolysis," *Biochem. J.* 1:314:701-707, 1996.

Walsh et al., "Amyloid β-Protein Fibrillogenesis. Detection of a Protofibrillar Intermediate," *J. Biol. Chem.* 272(35):22364-22372, 1997.

Walsh et al., "Amyloid β-Protein Fibrillogenesis. Structure and Biological Activity of Protofibrillar Intermediates," *J. Biol. Chem.* 274(36):25945-25952, 1999.

Extended European Search Report for European Patent Application No. 08019830.2, May 31, 2010.

Response to Communication in European Patent Application No. 07747965.7-1222, Sep. 11, 2009.

Communication from European Patent Application No. 07747965.7, Nov. 17, 2009.

Response to Communication in European Patent Application No. 07747965.7-1222, Jan. 29, 2010.

Invitation Pursuant to Article 94(3) and Rule 71(1) EPC from European Patent Application No. 07747965.7-1222, Mar. 26, 2010.

Appellant's Statement of Grounds of Appeal together with a Main Request, First Auxiliary Request and Second Auxiliary Request for consideration by the Appeal Board, and a signed Declaration by Professor Dominic Walsh of the Conway Institute, Dublin, IE as filed in European Patent Application No. 01945896.7, Jan. 15, 2010.

WO 05/123775 A1, pp. 7-8, published Dec. 29, 2005.

Communication as issued by European Patent Office regarding extended European Search Report for European Patent Application No. 07747965.7, dated May 13, 2009.

Search Report and Written Opinion as issued by Intellectual Property Office of Singapore regarding Singapore Patent Application No. 200803655-0, dated Oct. 8, 2009.

Declaration of Pär Gellerfors, dated Nov. 28, 2010.

Communication of Notice of Opposition for European Patent Application No. 07747965.7, dated Oct. 13, 2011.

Notice of Opposition to a European Patent for European Patent No. 2,004,688 as filed by Acumen Pharmaceuticals, dated Sep. 22, 2011.

Opposition Against European Patent No. 2,004,688 as filed by Acumen Pharmaceuticals dated Sep. 22, 2011, including (1) Facts and arguments in support of opposition: Annex 1; (2) Annex 2.

Evidence D1-D6 included in Opposition Against European Patent No. 2,004,688 as filed by Acumen Pharmaceuticals dated Sep. 22, 2011.

Evidence D7-D11 included in Opposition Against European Patent No. 2,004,688 as filed by Acumen Pharmaceuticals dated Sep. 22, 2011.

Mouse n, non-immunized mouse (control)

Figure 4:
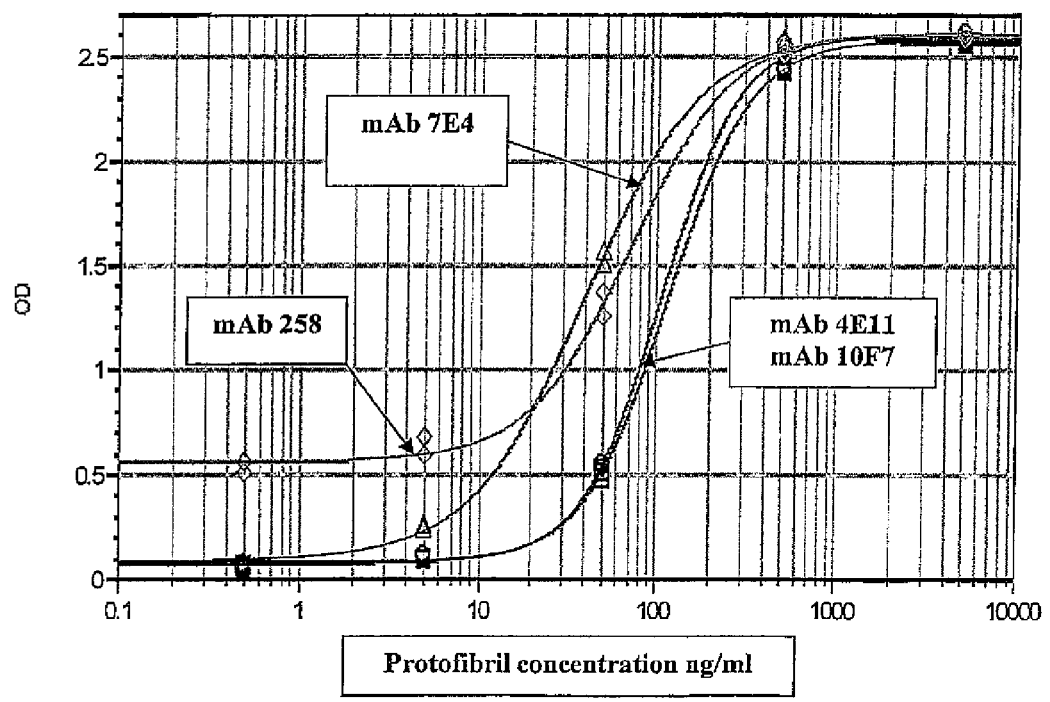
Figure 4:
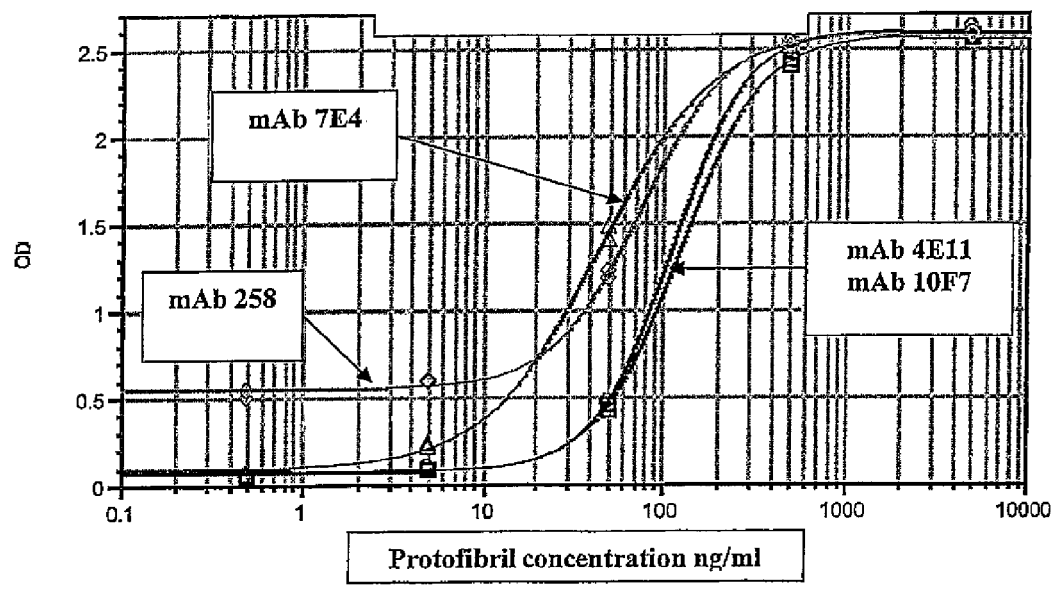

FIG. 4, A
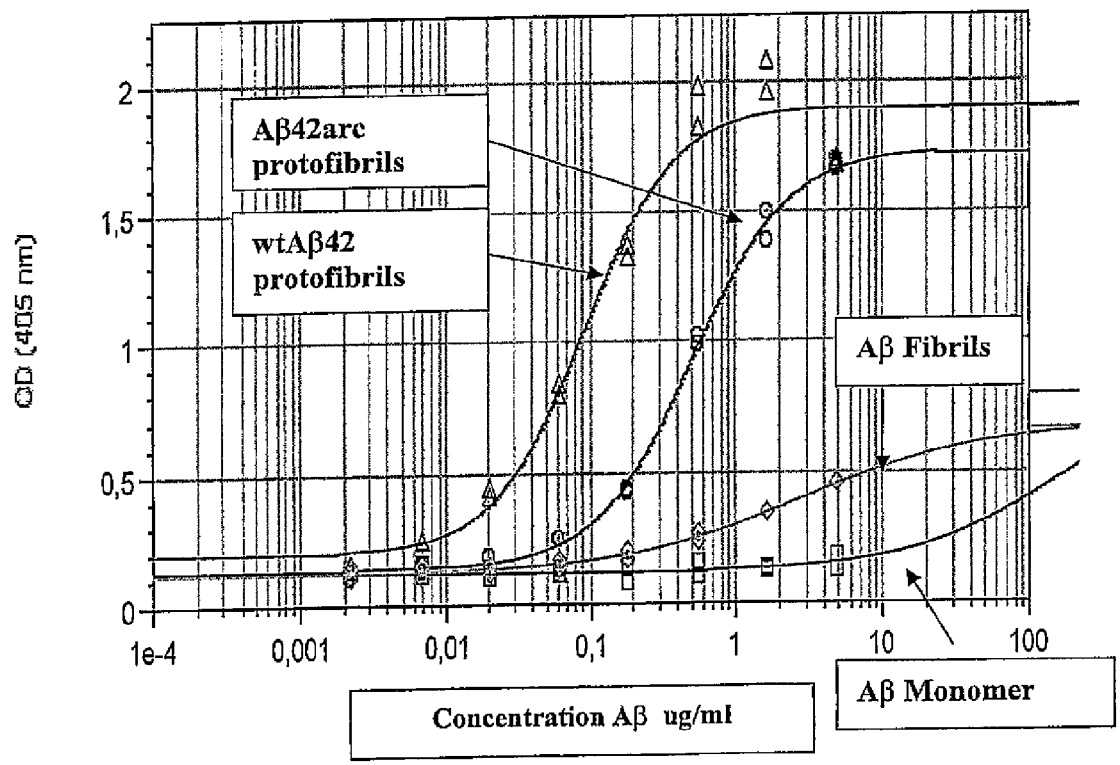

Titration by a sandwich-ELISA of 4 monoclonal antibodies ( 258, 7E4, 4E11 and 10F7) against wtAβ42 protofibril concentration.

Titration by a sandwich-ELISA of 4 monoclonal antibodies (258, 7E4, 4E11 and 10F7) against wtAβ42 protofibril concentration.

SEQUENCE LISTING

<160> NUMBER OF SEQ ID NOS: 1

<210> SEQ ID NO 1

```
<211> LENGTH: 42
<212> TYPE: PRT
<213> ORGANISM: Homo Sapiens

<400> SEQUENCE: 1

Asp Ala Glu Phe Arg His Asp Ser Gly Tyr Glu Val His His Gln Lys
1               5                   10                  15

Leu Val Phe Phe Ala Gly Asp Val Gly Ser Asn Lys Gly Ala Ile Ile
            20                  25                  30

Gly Leu Met Val Gly Gly Val Val Ile Ala
            35                  40
```

ANTIBODIES SPECIFIC FOR SOLUBLE AMYLOID BETA PEPTIDE PROTOFIBRILS AND USES THEREOF

CROSS-REFERENCE TO RELATED APPLICATIONS

This application is the U.S. national stage filing under 35 U.S.C. §371 of international application PCT/SE2005/000993, filed Jun. 21, 2005, which claims benefit of Swedish Patent Application 0401601-0, filed Jun. 21, 2004.

1. FIELD OF INVENTION

This invention pertains to the diagnosis, prevention and treatment of neurodegenerative diseases, in particular Alzheimer's disease, and other similar disease. More precisely, to antibodies that specifically bind amyloid beta protein (Aβ) in its protofibril conformation.

2. BACKGROUND OF THE INVENTION

Alzheimer's disease (AD) is a progressive and irreversible neurodegenerative disorder causing cognitive, memory and behavioural impairments. It is the most common cause of dementia in the elderly population affecting roughly 5% of the population above 65 years and 20% above 80 years of age. AD is characterized by an insidious onset and progressive deterioration in multiple cognitive functions. The neuropathology involves both extracellular and intracellular argyrophillic proteineous deposits. The extracellular deposits, referred to as neuritic plaques, mainly consist in amyloid beta protein (Aβ) surrounded by dystrophic neurites (swollen, distorted neuronal processes). Aβ within these extracellular deposits are fibrillar in their character with a β-pleated sheet structure. Aβ in these deposits can be stained with certain dyes e.g. Congo Red and display a fibrillar ultrastructure. These characteristics, adopted by Aβ in its fibrillar structure of neuritic plaques, are the definition of the generic term amyloid. The classic intracellular AD pathologic lesion is the neurofibrillary tangle (NFT) which consists of filamentous structures called paired helical filaments (PHFs) composed of twisted strands of hyperphosphorylated microtubule-associated protein tau. Frequent neuritic plaques and neurofibrillary tangle deposits in the brain are diagnostic criteria for AD, as carried out post mortem. AD brains also display macroscopic brain atrophy, nerve cell loss, local inflammation (microgliosis and astrocytosis) and often congophilic amyloid angiopathy (CAA) in cerebral vessel walls.

Two forms of Aβ peptides, Aβ40 and Aβ42, are the dominant species in AD neuritic plaques (Masters 1985), while Aβ40 is the prominent species in cerebrovascular amyloid associated with AD (Glenner 1984). Enzymatic activities allow Aβ to be continuously formed from a larger protein called the amyloid precursor protein (APP) in both healthy and AD afflicted subjects in all cells of the body. Two major APP processing events through β- and γ-secretase activities enables Aβ production, while a third enzyme called o-secretase activities prevents Aβ generation by cleavage inside the Aβ sequence (Selkoe, 1994; U.S. Pat. No. 5,604,102). The Aβ42 is a forty two amino acid long peptide i.e. two amino acids longer at the C-terminus, as compared to Aβ40. Aβ42 is more hydrophobic, and does more easily aggregate into larger structures of Aβ peptides such as Aβ dimers, Aβ tetramers, Aβ oligomers, Aβ protofibrils or Aβ fibrils. Aβ fibrils are hydrophobic and insoluble, while the other structures are all less hydrophobic and soluble. All these higher molecular structures of Aβ peptides are individually defined based on their biophysical and structural appearance e.g. in electron microscopy, and their biochemical characteristics e.g. by analysis with size-exclusion chromatography/western blot. These Aβ peptides, particularly Aβ42, will gradually assemble into a various higher molecular structures of Aβ during the life span. AD, which is a strongly age-dependent disorder, will occur earlier in life if this assembly process occurs more rapidly. This is the core of the "amyloid cascade hypothesis" of AD which claims that APP processing, the Aβ42 levels and their assembly into higher molecular structures is a central cause of AD. All other neuropathology of AD brain and the symptoms of AD such as dementia are somehow caused by Aβ or assembled forms thereof.

Aβ can exist in different lengths i.e. 1-39, 1-40, 1-42 and 1-43 and fragments sizes i.e. 1-28, 3-40/42, 11-40/42, 17-40/42 and 25-35. All these peptides can aggregate and form soluble intermediates and insoluble fibrils, each molecular form having a unique structural conformation and biophysical property. Monomeric Aβ1-42 for example, is a 42 amino acid long soluble and non-toxic peptide, that is suggested to be involved in normal synapse functions. Under certain conditions, the Aβ1-42 can aggregate into dimers, trimers, tetramers, pentamers up to 12-mer and higher oligomeric forms, all with its distinct physicochemical property such as molecular size, EM structure and AFM (atomic force microscopy) molecular shape. An example of a higher molecular weight soluble oligomeric Aβ form is the protofibril (Hartley 1999, Walsh 1999), which has an apparent molecular weight>100 kDa and a curvelinear structure of 4-11 nm in diameter and <200 nm in length. It has recently been demonstrated that soluble oligomeric Aβ peptides such as Aβ protofibrils impair long-term potentiation (LTP) (Hartley, 1999), a measure of synaptic plasticity that is thought to reflect memory formation in the hippocampus (Walsh 2001). Furthermore, oligomeric Arctic Aβ peptides display much more profound inhibitory effect than wtAβ on LTP in the brain, likely due to their strong propensity to form Aβ protofibrils (Klyubin 2003).

There are also other soluble oligomeric forms described in the literature that are distinctly different from protofibrils. One such oligomeric form is ADDL (Amyloid Derived Diffusible Ligand) (Lambert 1998). AFM analysis of ADDL revealed predominantly small globular species of 4.7-6.2 nm along the z-axis with molecular weights of 17-42 kDa. (Stine 1996). Another form is called ASPD (Amyloidspheroids). ASPD are spherical oligomers of Aβ1-40. Toxicity studies showed that spherical ASPD>10 nm were more toxic than lower molecular forms (Hoshi 2003). The Aβ fibril as the main neurotoxic species is inconsistent with the poor correlation between neuritic plaque density and AD dementia score and also with the modest signs of neurodegeneration in current APP transgenic mice. Soluble neurotoxic Aβ-intermediate species and their appropriate subcellular site of formation and distribution could be the missing link that will better explain the amyloid hypothesis. This idea has gained support from recent discovery of the Arctic (E693) APP mutation, which causes early-onset AD (US 2002/0162129 A1; Nilsberth et al., 2001). The mutation is located inside the Aβ peptide sequence. Mutation carriers will thereby generate variants of Aβ peptides e.g. Arctic Aβ40 and Arctic Aβ42. Both Arctic Aβ40 and Arctic Aβ42 will much more easily assemble into higher molecular structures (protofibrils) that are soluble and non-fibrillar. Thus the pathogenic mechanism of the Arctic mutation suggests that the soluble higher molecular protofibrils are causing AD.

2.1 Diagnosis of Alzheimer's Disease 2.1.1 Clinical Diagnosis

The clinical diagnosis of Alzheimer's disease (AD) is difficult to make, especially in early stages of the disease. Today, the diagnosis is based on a typical medical history combined with the exclusion of other causes of dementia. Clinical centres with high specialization can have a diagnostic accuracy of 85-90% compared with the neuropathological diagnosis. In the early stages of the disease the clinical picture is vague and definite diagnostic markers have not yet been identified (McKhann 1984). The development of biochemical diagnostic markers is important for a number of reasons: to support the clinical diagnosis, to allow clinicians to give adequate information to patients and their relatives, to initiate pharmacological treatment and care-giving, and in various aspects of clinical research.

2.1.2 Amyloid β-Peptide

Pathogenic mutations in the APP and presenilin (PS) genes have been discovered in families with early-onset AD inherited as a dominant trait (Hardy 1992). The effects of some of these mutations are now fairly well understood. The Swedish AD mutation (Mullan 1992; Axelman 1994; Lannfelt 1994) has revealed one pathogenic mechanism for the development of AD. When a cDNA construct with this mutation was transfected into human cell-lines it gave rise to approximately six times higher release of soluble Aβ (Citron 1992, Cai 1993). Furthermore, fibroblasts from individuals with the Swedish mutation secreted three times more Aβ into the media compared to fibroblasts from non-carriers (Johnston 1994). Overproduction of Aβ therefore seemed to be an important factor in the disease pathogenesis in this Swedish family. Thus, it was expected that Aβ levels measured in cerebrospinal fluid (CSF) from family members would differentiate carriers from non-carriers of the mutation. However, no difference was found in levels of total Aβ between the groups (14.5±3.3 ng/ml versus 14.9±2.3 ng/ml) (Lannfelt 1995). One explanation for this result may be that Aβ is cleared from CSF by aggregating to amyloid in the brain. However, there was a strong correlation between duration of dementia and decreasing Aβ levels. These measurements were done with antibodies recognizing soluble monomeric Aβ. With protofibril specific monoclonal antibodies more accurate measurements of the toxic species will be possible.

2.1.3 Aβ in Plasma

Aβ is found in a soluble form in plasma and other tissues (Seubert 1992), and not as previously presumed, only in the brains of AD cases. Aβ plasma levels in members of the Swedish mutation family revealed that both Aβ40 and Aβ42 were 2-3 times increased in mutation-carriers (Scheuner 1996). The proportion of Aβ42 of total Aβ was approximately 10% in both groups, which is in agreement with experiments performed in cell cultures with the Swedish mutation. Mutation-carriers below the age of expected onset of the disease had the same levels of Aβ as already affected cases. This indicates that APP mismetabolism may play an important role early in the pathogenesis of the disease.

2.1.4 Aβ42 in CSF in Alzheimer's Disease

ELISAs specifically measuring Aβ40 and Aβ42 in CSF in AD cases have given different results. Some researchers (Pirttilä 1994; Motter1995) have found decreased Aβ42 in AD, while one group have found elevated levels in cases early in the disease progression. The most demented cases in one study had all very low levels of Aβ42. In conclusion, Aβ42 is most likely increased early in the disease process and levels of Aβ42 and Aβ40 decreased during progression of the disease. The development of accurate biochemical markers of early AD is important especially when efficient pharmacological treatments will be available in the future. Pharmacological therapy should most likely be initiated at an early stage of disease, before severe brain damage has occurred. A therapy making it possible to prevent the progression of the disease to its later stages would therefore be much desired.

2.2 Prevention and Treatment of Alzheimer's Disease

Antibodies that are specific towards different conformations of Aβ, such as Aβ fibrils (O'Nuallain 2002), micellar Aβ (Kayed 2003), ADDL (M93, M94) (Lambert 2001) have also been described.

Several pre-clinical studies in transgenic animal models have shown decreased plaque burden and improvements in memory function after active or passive immunization with antibodies raised against fibrils (Shenk 1999, Janus 2000, Morgan 2000, Weiner 2000, Sigurdsen 2001). Since fibrils are present in pathological deposits occurring late in the Alzheimer disease process, the Shenk antibodies may only be used to slow the progression of Alzheimer's disease when it has already reached its later stages.

Recently, a phase II clinical trial in Alzheimer patients with mild to moderate dementia was performed by ELAN Pharmaceuticals with their vaccine AN 1792, which is an aggregated preparation of human wtAβ42. The study had to be stopped due to side effects in 5% of the patients. The side effect was considered to be due to T-lymphocyte-induced meningioencephalitis (Nicholl 2003). The drug targets of the ELAN vaccine were insoluble fibrils found in plaques inside the brain and deposits on the brain blood vessel walls (Congophilic Amyloid Angiopathy, CAA), which are common features of Alzheimer's disease. Thus, an immune response towards insoluble fibrils could be responsible for the invasive inflammation in the brain blood vessel walls leading to meningioencephalitis.

WO02/203911 disclose the discovery of the Arctic mutation in a Swedish family leading to early onset of Alzheimer's disease (55.6 years). The Arctic mutation (Glu>Gly), which is located at position 22 in the beta amyloid peptide (Aβ), in combination with various experiments led to the insight that the Aβ peptide was much more prone to oligomerize and form protofibrils compared to wild type Aβ40. The discovery indicated for the first time that the protofibril is a central component in the disease process, and that AD could be treated by reducing the amount of protofibrils in the brain. This unique property of the Arctic mutation could then be used to generate protofibrils. WO02/203911 then suggested that said protofibrils could be used to immunize a mouse or other animal, in order to generate antibodies, after which any protofibril-specific monoclonal antibody could identified be screening. Said antibodies should then be specific towards an Aβ peptide of SEQ ID No 1 (page 7, third paragraph), i.e. a peptide carrying the Arctic mutation and having a protofibril conformation.

Thus, in view of the prior art techniques for preventing and treating Alzheimer's disease, there is a need for a technique that enables earlier detection of markers of Alzheimer's disease. If said markers could be prevented without causing negative side-effects, this would be a means to prevent and treat Alzheimer's disease at an early stage. Any treatment of Alzheimer's disease that would reduce the amount of protofibrils in the brain of AD patients, would be of significant therapeutic value.

3. DESCRIPTION OF THE INVENTION

Protofibrils occur early in Alzheimer's disease, when little brain damage has occurred. An antibody treatment that reduce protofibril levels in the brain will save the brain from neuronal destruction and hence be more advantageous for Alzheimer patients. The present invention describes the development of such therapeutic protofibril specific antibodies.

According to one aspect, the present invention relates to antibodies that have the property to bind both wild type Aβ42/40 and Aβ42/40arc protofibrils (conformation-specific antibodies) and which are suitable for development into pharmaceuticals for Alzheimer's disease, targeting wild type Aβ42/40 protofibrils. Current ideas in the field of Alzheimer's disease research is that Aβ fibrils are the main cause of the disease. Hence, the approach of the present invention contradicts the general opinion within the field.

According to another aspect, the present invention also relates to a composition comprising said antibody and optionally a carrier or excipient.

To immunise and screen for conformation-specific anti-protofibril antibodies, it is necessary to produce pure Aβ42arc and Aβ42 protofibrils (>95% degree of purity). In order to obtain said pure protofibril preparation, it is also necessary to be able to stabilise the protofibrils, such that they stay protofibrils and do not separate into monomers or aggregate into fibrils. It is also necessary to find a solvent that made it possible to separate the protofibrils by column chromatography. Another necessity is the ability to test said purity before immunisation. The above-mentioned abilities are essential, since the degree of purity of the antigen (protofibrils) decide the possibility to produce conformation-specific anti-protofibril antibodies, which in turn decide the possibility to screen for antibodies with useful specificity. Should the preparation for example contain 50% Aβ monomer and 50% Aβ protofibril, it is only possible to claim that the antibody binding said preparation may bind both forms or only one. All of said necessary features are provided by the present invention.

The above-mentioned features were not possible when WO02/203911 was filed. The HPLC analysis method disclosed it the present application or any other analysis method had not been developed, wherefore it was not possible to determine whether the Aβ42arc peptide actually formed protofibrils, probably due to the lack of binding to protofibrils. It was only a hypothesis at the time. The major reasons why WO02/203911 could not analyse and purify protofibril preparation to a degree of purity of >95%. Also, to the fact that they did not know how to stabilise protofibrils. In that connection, it should also be mentioned that protofibrils are very difficult to handle in comparison with for example Aβ40 peptides. Aβ42, but in particular the Aβ42βrc peptide, is extremely difficult to handle, since they stick to test tubes and columns and aggregate into fibrils. The latter problems has been solved by the present invention by the provision of methods to stabilise the protofibrils involving low temperatures and selected solvents. WO02/203911 also had no means for testing the purity of the protofibrils before immunisation. This is possible with the present invention by the provision of a new HPLC (size exclusion) method. In addition to this, WO02/203911 did not provide any means to check the protofibril specificity of the screened antibodies. The present invention makes this possible by the provision of a new Elisa method. WO02/203911 could only produce impure and transient Aβ40arc protofibrils, not useful for monoclonal development of protofibril specific antibodies (WO02/203911 only describes analysis of Aβ40 and Aβ40Arc peptides, see Example 3).

The antibodies according to the present invention are particularly suitable for treating Alzheimer's disease since they will: i) target and eliminate the most toxic AZ form (protofibril), ii) provide an opportunity to treat the disease early since protofibrils develops early in the disease process, iii) avoid side-effects since the will not significantly cross-react with Aβ fibrils present in the blood vessel wall of the brain (CAA=Congophilic Amyloidogenic Angiopathy).

The antibodies according to the present invention may be human or humanised, monoclonal or polyclonal. The present invention also relates to biologically active fragments of said antibodies, with the proviso that they still have the claimed properties.

The Aβ protofibril specific antibodies according to the present invention can also be used to quantitate wild type Aβ42/40 protofibrils in biological fluids, thus the antibodies will be suitable for clinical diagnosis at an early stage of the disease and suitable as a biomarker to monitor efficacy in clinical studies.

Furthermore, the invention describes procedures to generate wild type Aβ42 and Aβ42arc protofibrils as antigens for immunization and for reagents to screen for antibodies that binds Aβ42arc and wild type Aβ42 protofibrils. Antigen (protofibril) purity is very important to determine in antibody screening experiments, since it affects antibody specificity determinations by ELISA.

To assess the purity of antigen (Aβ42arc and wild type Aβ42 protofibrils) preparation, a size exclusion HPLC method has been developed. The HPLC method invented uses a detergent, with low optical interference in chromatography. The detergent has the advantage that it eliminates interactions of Aβ42arc and wild type Aβ42 protofibrils with the column matrix, preventing loss of material and material from adhering to the column, and erroneous estimations of protofibril purity. Furthermore, the detergent is compatible with Aβ protofibrils and does not solubilize them into Aβ monomers or alter their biological profile. Polysorbate (Tween) has been found to be a suitable detergent, in particular Polysorbate-80 (Tween-80). Other detergents with similar properties are also useful.

The antibody according to the present cross-reacts less than 50% with Aβ fibrils. Said antibody can detect both wild type Aβ protofibrils and Arctic Aβ protofibrils in an ELISA in a concentration range of 1000-10 ng/ml (see Example 5 and FIGS. 4A-C). In an optimised ELISA or by other detection systems with higher sensitivity, for example proximity ligation, said detection level could probably be brought down to a detection level of 1-0.1 ng/ml.

The present invention provides a method to raise antibodies that are specific to amyloid β (Aβ) protofibrils (high molecular weight soluble non-fibrillar Aβ oligomers). The antibodies are raised against Aβ in its protofibril conformation. These antibodies will be administered to AD patients to reduce protofibril levels in the brain, which will be of significant therapeutic value.

The lowering of protofibril levels might occur through the elimination of the antigen when bound to an antibody, through microglia-mediated phagocytosis. This is a well documented biological process, which occurs through the binding of the antibody's constant region (Fc) to an Fc receptor on microglial cells. Binding induces phagocytosis (internalisation and destruction) of the antibody and its bound antigen (protofibril) leading to reduced levels of protofibrils in the brain. Other non-Fc receptor mediated processes might also occur to eliminate the antigen (protofibril).

Another aspect of the invention pertains to a method to synthesize Aβ protofibrils which are to be used as antigen for immunization. The synthesis can be made from wild type Aβ (wtAβ) or alternatively, from non-wild type, mutated or modified forms of Aβ. In a preferred embodiment of the invention, but not limited to said embodiment, the synthesis is initiated by dissolving wtAβ1-42 in a dissociating agent, for example NaOH, to achieve a homogenous Aβ solution, of about 50-500 uM in peptide concentration, but not limited to this concentration. Alternative agents with dissociating capacity are for example dimethylsulfoxide, DMSO; hexafluoroisopropanol, HFIP; trifluoroacetic acid, TFA. Wild type protofibrils can also be made from wtAβ peptides of different lengths i.e. wtAβ1-39, wtAβ1-40, wtAβ1-43 or N-terminal truncated forms of these peptides. The truncation can be 1-10 amino acids, giving wtAβ forms such as: wtAβ2-42, wtAβ3-42, wtAβ4-42, wtAβ5-42 and so on. The dissolved wtAβ1-42 peptide is subsequently neutralized by PBS or similar physiological buffer and incubated at higher temperature, preferably 37° C., for a period of time sufficient for protofibril-formation to occur, for example over night. This will yield wild type Aβ protofibrils. The invention also provide a molecular size (molecular weight) determination method to assess protofibril formation and purity, preferably, but not limited to, a size-exclusion chromatographic method (SEC).

The method of synthesizing pure wild type (wtAβ42) protofibril antigen, comprises the steps of dissolving an wtAβ42 by using a dissociating agent, such as NaOH (pH>10), dimethylsulfoxide, DMSO; hexafluoroisopropanol, HFIP; trifluoroacetic acid and TFA, to achieve a monodisperse solution, neutralizing the solution by PBS (pH 7-8) or similar biocompatible buffers, to achieve a physiological solution, incubating the neutralized wtAβ42 peptide solution at an elevated protein concentration between 1-1000 uM, preferably 440 uM, for 6 hours or longer at 20-40° C., preferably 37° C., to form Aβ42wt protofibrils, diluting the protofibrils to approximately 1-500 uM, preferably 50 uM centrifuging at sufficient speed and time to sediment wtAβ42 fibrils, which normally takes 5 minutes at 17.000×g at +4° C., assessing the purity of the protofibril preparation by HPLC to control that the purity is >95%, using for example size exclusion HPLC, using a physiological buffer such as PBS at neutral pH as running buffer, including a detergent, such as Polysorbate (Tween), or similar detergent, to avoid sticking of the protofibrils to the column matrix and dissociation.

Another aspect of the invention pertains to the synthesis of non-wild type Aβ protofibrils using Aβ1-42, Aβ1-41, Aβ1-40 or Aβ1-39 or N-terminal truncated forms (1-10 truncations) with either the Arctic (G22E) mutation (U.S. Ser. No. 09/899, 815), the Dutch mutation (E22Q), the Flemish (A21G) mutation, the Italian (E22K) mutation, the Iowa (D23N) mutation, and combinations thereof. In a preferred embodiment of the invention Aβ42arc peptide (i.e., comprising the arctic mutation) is used. The method to make Aβ42arc protofibrils is similar to that for wtAβ42 protofibrils except that Aβ42arc protofibrils are not incubated at 37° C. over night since they are spontaneously formed after the neutralization step.

The method of synthesizing pure Aβ42arc protofibril antigen comprises the steps of dissolving an Aβ42arc peptide by using a dissociating agent, such as NaOH (pH>10), dimethylsulfoxide, DMSO; hexafluoroisopropanol, HFIP; trifluoroacetic acid and TFA to achieve a monodisperse solution, neutralizing the solution by PBS (pH 7-8) or similar biocompatible buffers, to achieve a physiological solution, stabilizing the spontaneously formed protofibrils by keeping them at below 20° C., preferably at 0-5° C., centrifuging the protofibrils, at the same temperature as in the stabilising step, at a sufficient speed and time to sediment Aβ42arc fibrils, which normally takes 5 minutes at 17.000×g at +4° C., assessing the purity of the protofibril preparation by HPLC to control that the purity is >95%, using for example size exclusion HPLC, using a physiological buffer such as PBS at neutral pH as running buffer, including a detergent, such as Polysorbate (Tween), or similar detergent, to avoid sticking of the protofibrils to the column matrix and dissociation.

Another aspect of the invention pertains to the development of antibodies that cross-react with wild type Aβ42 protofibrils after immunization with Aβ42arc protofibrils.

Another aspect of the invention pertains to a method to stabilize Aβ protofibril and where stabilization can be assessed by size-exclusion chromatography (SEC). Aβ protofibrils elutes after 12-13 minutes in a uniform peak on a Superdex 75 or similar size-exclusion column. Conformation stability can also be assessed by staining with Congo Red and (electron microscopy), where protofibrils attain a curve-linear structure of 6-10 nm in diameter and <200 nm in length. Lowered temperature has a significant effect on Aβ protofibril conformational stability, Samples should preferably be kept below 20° C., preferably below 5° C., and most between 0° C. and 5° C. Furthermore, agents that decrease the polarity or surface tension or increase viscosity have stabilizing effects on Aβ protofibril conformation. For example, 10-50% glycerol or 0.6-5% Polysorbate (Tween), have stabilizing effects on Aβ protofibrils. These agents and treatments can be added to the Aβ protofibril preparation preferably after the neutralization step in the method to synthesize Aβ protofibrils described above. Addition of these agents before this step is also possible. Increased stability of protofibrils is advantageous when developing monoclonal antibodies and when Aβ protofibrils are used as reagents in immunoassays, such as ELISA, radio-immunoassay (RIA), Western blotting or dot blotting.

The method of stabilizing the Aβ protofibrils includes mixing them with an agent that decreases the solvent polarity or one that lowers the surface tension, such as glycerol or Polysorbate (Tween), or a combination of said agents. The stabilisation can also be achieved by keeping the protofibrils at a temperature below 20° C., preferably 0-5° C. Said methods can also be combined.

The invention further pertains to the use of anti-Aβ protofibril specific antibodies for determinations of Aβ protofibrils in human and animal tissues, for example, cerebrospinal fluid, blood, serum, urine and brain tissue, but is not limited to these tissues, providing for a possible diagnostic method for Alzheimer's disease. Suitable methods for assaying Aβ protofibrils in these tissues as well as in cell cultures using an anti-Aβ protofibril antibody are immunoassays such as ELISA, RIA, Western blotting dot blotting or proximity ligation. The method would be suitable to follow treatment efficacy (protofibril reduction) in clinical trials and suitable as a diagnostic test for Alzheimer's disease or Down's syndrome.

The method of diagnosing or monitoring Alzheimer's disease (AD) or Down's syndrome comprises the steps of labelling the antibody according to the present invention with an agent that can generate a measurable signal, administering said antibody according to a subject having or suspected of having AD or Down's syndrome, measuring the amount of protofibrils bound to the antibody by measuring the signal generated by the agent.

The invention further pertains to the use of an anti-Aβ protofibril antibody in imaging for detection, localization and quantitation of Aβ protofibrils in human and animal tissues. The anti-Aβ protofibril antibody could be label with a radioactive ligand such as $I^{131}$, $C^{14}$, $H^3$ or $Gallium^{68}$, but it is not limited to these radioisotopes, for detection purposes. In addition to labelling with radioactive markers, DNA, fluorescent molecules, enzymes which converts a substrate such that its absorbance can be measured, could also be used. The method will be suitable as a diagnostic tool for Alzheimer's disease or Down's syndrome, Lewybody dementia, vascular dementia, and other neurodegenerative disorders.

A further aspect of the invention pertains to the use of an anti-Aβ protofibril antibody for the prevention or treatment of Alzheimer's disease. Pre-clinical studies in transgenic animal models have demonstrated effects on plaque burden (Bard 2000), reversal of memory deficits (Dodard 2002) and drainage of Aβ from CNS after anti-Aβ antibody treatment. However, the antibodies used in these studies have not been specific to Aβ protofibrils. Administration of an anti-Aβ protofibril antibody, with no or little cross-reactivity towards Aβ monomers and fibrils would be particular suitable for treatment and prevention of Alzheimer's disease. Firstly, it would not bind significantly to fibrillar forms of Aβ and avoid interaction with fibrillar deposits which are prevalent in blood vessel walls, avoiding sever immunoreactions with concomitant serious brain inflammation and encephalitis, which was encountered in the ELAN vaccination study (see at the end of the Background) with their vaccine AN-1792 (Nicoll 2004). Secondly, an anti-Aβ protofibril antibody with low Aβ1-40 and Aβ1-42 monomer cross-reactivity would not bind and interfere with their normal biological functions, thus avoiding side effects.

In said method of prevention or treatment of Alzheimer's disease or Down's a subject having or suspected of having Alzheimer's disease, Down's syndrome, Lewybody dementia, vascular dementia, and other neurodegenerative disorders, is administered the antibody or composition according to the present invention.

The invention also provides a technique whereby anti-Aβ protofibril antibodies can be used to identify and select for epitopes present on Aβ protofibrils but less on Aβ monomers and Aβ fibrils or other Aβ conformational forms. The method is general and is applicable to other amyloids forming protofibrils such as, but not limited to, islet amyloid protein peptide (IAPP, amylin) associated with Type-2 diabetes, prion protein (PrP), alpha-synuclein (Parkinson). Considering the central role of amyloid beta (Aβ) protofibrils in Alzheimer's disease, these antibodies can be used to diagnose or treat Alzheimer's disease. There is a need for a method that specifically can determine protofibrils in different human and animal tissues such as cerebral spinal fluid (CSF), plasma, blood, urine and brain tissue, but is not limited to these tissues. Such a method could be used as a diagnostic method for Alzheimer's disease but also for similar diseases that forms amyloid protofibrils including Parkinson (alpha-synuclein) (Sthilerman 2002), Type-2 diabetes (Islet amyloid polypeptide, IAPP) (WO03/092619 A2), and Creutzfeldt-Jacob Disease and the corresponding animal disease called mad cow disease (Prion protein) (DeMarco 2004), but is not limited to these diseases.

According to another aspect, the present invention relates to the use of anti-Aβ protofibril antibodies for in vitro or in vivo screening of substances that inhibit or modulate Aβ protofibril levels and/or activity in cell cultures or animal models, being potential Alzheimer drugs. Suitable screening systems would be, but are not limited to, cell cultures (HEC or neuroblastoma cells) or for example the Thy-1 APPSweArc transgenic mouse model, (Nilsson L. et al. Swedish patent application 0400707-6, 2004) that expresses human Amyloid Precursor Protein (APP) with the Arctic mutation (E693G) providing increased production of Aβ protofibrils. Alzheimer drug candidates can be administered to these cell cultures or transgenic animal models and their effects on Aβ protofibril levels measured by an immunoassay, using an anti-Aβ protofibril antibody as reagent. Such method would be ideally suitable for identifying potent Alzheimer drug candidates.

Said method for in vitro or in vivo screening of substances that inhibit or modulate Aβ protofibril levels and/or activity in cell cultures or animal models, comprises the steps of administering potential drug candidates to a cell culture or an animal model, administering the antibody according to any the present invention, labelled with an agent that can generate a measurable signal, to said cell culture or animal model, evaluating the effect of said drug candidates by measuring the amount of protofibrils bound to the antibody by measuring the signal generated by the agent.

According to another aspect, the present invention relates to a method of detecting Aβ protofibrils in vitro, comprising labelling the according to the present invention with an agent that can generate a measurable signal, contacting said antibody or the composition comprising the antibody with a biological sample suspected of containing soluble protofibrils, measuring the amount of protofibrils bound to the antibody by measuring the signal generated by the agent. Said method may be an immunoassay. The biological samples tested may be selected from plasma, CSF, brain and other tissues of animal or human origin. The labelling includes labelling with radioactive markers, DNA, fluorescent molecules, enzymes which converts a substrate such that its absorbance can be measured.

All percentages in the description relates to percent volume, unless stated otherwise.

4. DESCRIPTION OF THE DRAWINGS

FIG. 1. Size Exclusion Chromatography (SEC) of Human Monomer Aβ40, Protofibril Aβ42Arc, Protofibril wtAβ42 and Fibril wtAβ42 Preparations Human Aβ monomers and Aβ protofibrils are eluting in 19-20 minutes and at 12-13 minutes, respectively. The protofibril preparations (B and C) are essentially free (<3%) from contamination of other conformational Aβ forms. The analysis of the fibril preparation (D) was done after centrifugation at 17.900×g for 5 minutes at room temp. The supernatant was analysed demonstrating the almost complete absence of any soluble Aβ forms in the fibril preparation.

Figure 2:
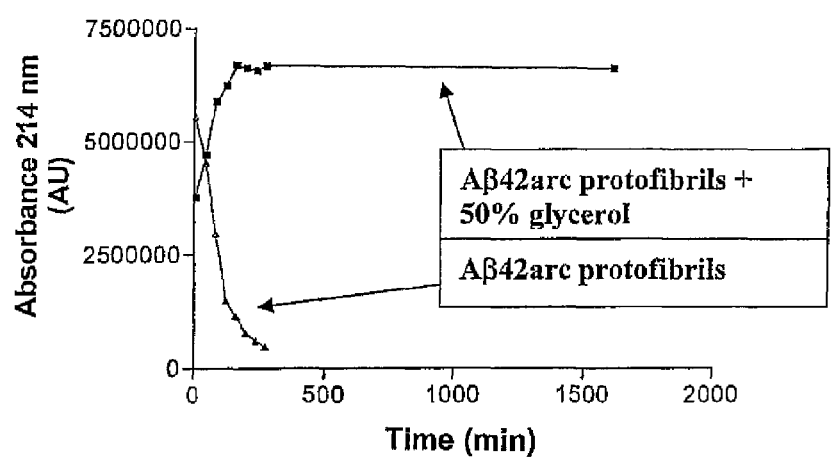
Figure 2:
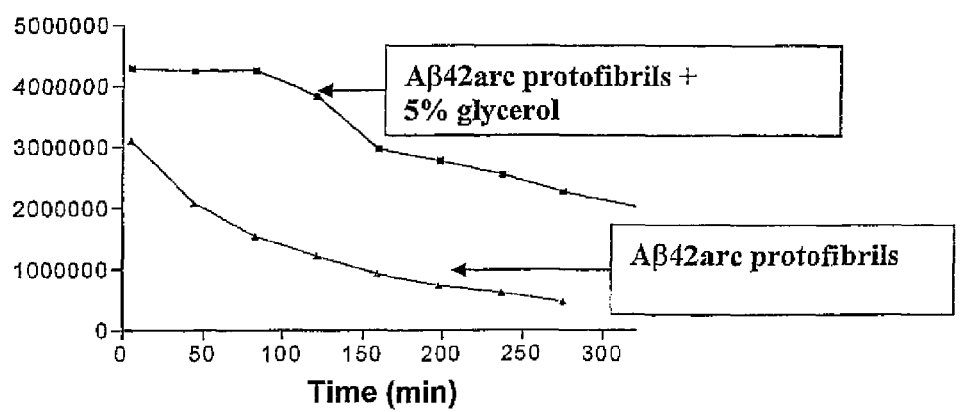
Figure 2:
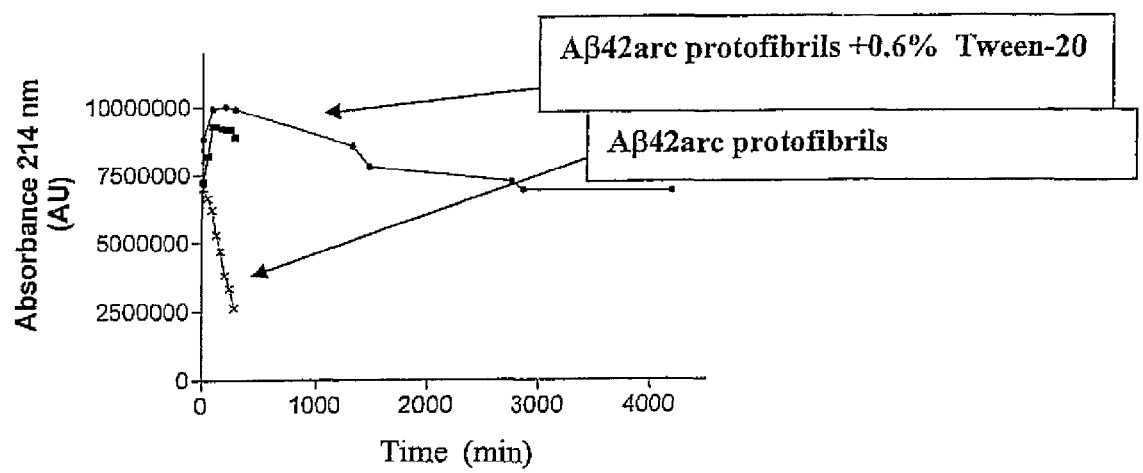
Figure 2:
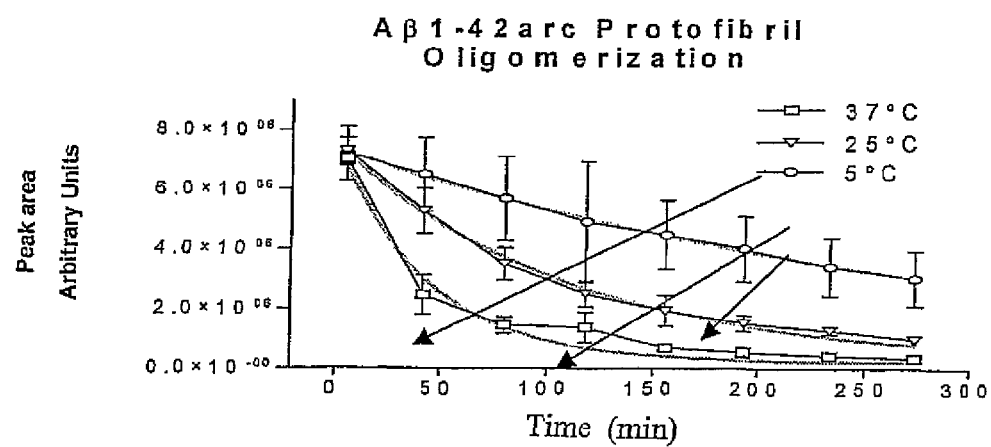

FIG. 2. Stability Study of Protofibrils

The stability of Protofibril Aβ42Arc and Protofibril wt42 preparations was measured by SEC. A conversion of protofibrils to fibrils was assessed by a decrease in the protofibril peak area (decreased absorbance (AU) at 214 nm elution time 12-13 minutes). The addition of 10-50% glycerol, 0.6% Tween-20 or storage at 0-5° C., all increased the protofibril stability significantly.

Figure 3:
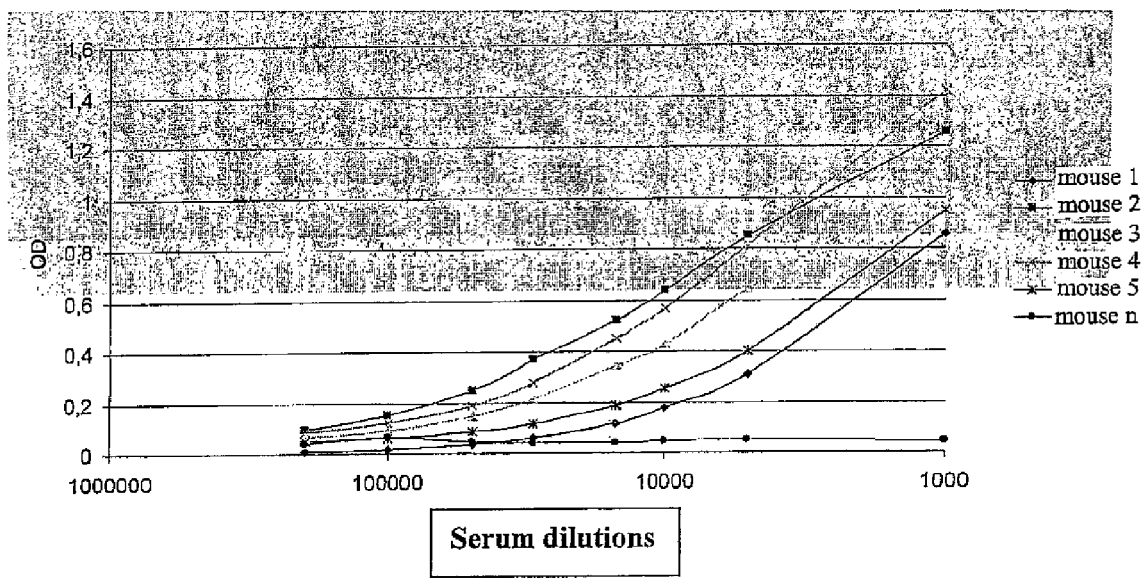

FIG. 3. Titration of Mouse Serum after Immunization with Protofibril wtAβ42

Mice were immunized with a protofibril wtAβ42 preparation in Freund complete adjuvant (first injection) and incomplete Freund adjuvant (5-6 boosters). Blood was collected and the antibody titers against Aβ protofibrils were determined. Mouse #2 and #4 showed the highest titers.

FIG. 4. Sandwich-ELISA Method using Anti-mAb 258 for Aβ Protofibril Determination mAb 258 was coated over night in a microtiterplate. Preparations of wtAβ42 protofibrils, Aβ42Arc protofibrils, wtAβ40 monomers and wtAβ42 fibrils were added in decreasing concentrations and incubated for 1 hour at +4° C. Secondary anti-Aβ antibody (6E10) was added. Finally, a detection ALP (alkaline phosphatase) conjugated antibody (anti-IgG) was added to each well. Detection was achieved by adding ALP substrate. The colour formation was measured in at 405 nm and 492 nm.

mAb 258 bound wtAβ42 protofibrils and slightly less Aβ42Arc protofibrils. No binding was observed to wtAβ40 monomers. The slight binding to wtAβ42 fibrils is probably due to a slight contamination with wtAβ342 protofibrils (see FIG. 1 D).

5. EXAMPLES

The following examples are provided for illustration and are not intended to limit the invention to the specific examples provided.

Example 1

Synthesis of Human Amyloid Beta Peptide (Aβ) of Different Conformations

Synthetic human wild type or mutant forms of Aβ1-42 or Aβ1-40 peptides were purchased from Polypeptide Laboratories GmbH. The peptides had been synthesized by a standard solid phase peptide synthesis procedure. The peptides were subsequently purified with RP-HPLC to a purity in the range of 90-95%. Alternative vendors producing Aβ peptides with similar purity are possible to use as well.

Synthesis of Human Wild Type Aβ1-40 Monomers

A synthetic wtAβ31-40 peptide was dissolved in 1 volumes of 10 mM NaOH pH>10, and 1 volume of cold 2×PBS (pH 7-8) to a concentration of 50 uM. The wtAβ1-40 monomer preparation was centrifuged at 17.900×g at +4° C. for 5 minutes prior to analysis (FIG. 1).

Synthesis of Human Wild Type Aβ1-42 Protofibrils

A synthetic wtAβ1-42 peptide was dissolved in 9 volumes of 10 mM NaOH pH>10, vortexed for 2 minutes and diluted with 1 volume of 10×PBS (pH 7-8). The final peptide concentration was at this point 443 uM. The peptide was further incubated over night at 37° C. After the overnight incubation, the peptide was further diluted with PBS to 50 uM. The sample was centrifuged for 17.900×g for 5 minutes prior to analysis and immunisation.

Synthesis of Human Aβ1-42Arc Protofibrils

A synthetic Aβ1-42Arc (E22G) peptide was dissolved in 1 volumes of 10 mM NaOH pH>10 and 1 volume cold 2×PBS (pH 7-8) to a final peptide concentration of 50 uM. The Aβ1-42Arc protofibrils were formed immediately and the Aβ1-42Arc protofibrils were stabilized by keeping the solution at 0-4° C. before analysis or immunization. The sample was centrifuged at 17.000×g for 5 minutes at +4° C. prior to analysis. Alternative ways to stabilize the Aβ1-42Arc protofibrils were to add glycerol to a final concentration of 5-50% or to add Tween-20 to a final concentration of 0.6%.

Synthesis of Human Wild Type Aβ1-42 Fibrils

A synthetic wtAβ1-42 peptide was dissolved in 1 volumes of double distilled water, vortexed for 2 minutes and diluted with 1 volume of 2×PBS (pH 7-8) and vortexed again for 2 minutes. The final peptide concentration at this point was 50 uM. The wtAβ1-42 protofibril preparation was incubated at 37° C., for 48 hours before analysis. The sample was centrifuged at 17.900×g for 5 minutes prior to SEC analysis. The supernatant was analysed after centrifugation. No centrifugation was performed when Aβ1-42 fibril preparations were analysed by ELISA or dot blotting.

Analysis of Aβ Preparation by Size Exclusion Chromatography (SEC)

A Merck Hitachi D-7000 HPLC LaChrom system, having a diode array detector (DAD) model L-7455 and a model L-7100 pump, was used for the chromatographic analysis of protofibril preparations in combination with a Superdex 75 PC3.2/30 column (Amersham Pharmacia Biotech, Uppsala, Sweden). The chromatographic system separates Aβ monomers from protofibrils, which are eluting at the void volume of the column. The column was equilibrated with 50 mM $Na_2HPO_4.NaH_2PO_4$ (pH 7.4) with 0.15 M NaCl (PBS) and 0.6% Tween 20 and eluted with the same buffer at a flow rate of 0.08 ml/min (pressure was 5-6 bars) at ambient temperature (22° C.). Ten (10 ul) of a 50 uM-100 uM Aβ sample was subjected analysis using a wavelength scan between 200-400 nm. Tween-20 was added to the sample to give a final concentration of 0.6% prior to chromatography. Data was extracted from measurements at 214 and 280 nm. Peak areas were integrated using Merck Hitachi model D-7000 Chromatography Data Station Software. FIG. 1 shows chromatograms of wtAβ1-40 monomer, wtAβ1-42 protofibril, Aβ1-42Arc protofibril and wtAβ1-42 fibril preparations.

Each preparation was essentially free (<3%) of other contaminating conformational Aβ forms except the wtAβ1-40 monomer preparation which contained 6.4% protofibrils (elution time 12-13 minutes).

Example 2

Protofibrils Specific Monoclonal Antibody Development

A standard procedure was used for monoclonal development. Mice were injected with wtAβ1-42 protofibril preparation. Alternatively, Aβ1-42Arc protofibrils could be used. Every wtAβ1-42 protofibril batch was assayed by SEC and Congo Red (binds β-sheet structures in proteins) before immunisation to ascertain protofibril purity and that the preparation contained β-sheet structure. The procedure used to immunise mice was a standard protocol involving s.c injections in the presence of Freund adjuvant. Each of six mice were immunized with 10 ug wtAβ1-42 protofibrils and subsequently boostered with 30 ug. The sample was mixed 1:1 with Freund complete adjuvant prior to the first injection. For subsequent 5 booster injections incomplete Freund adjuvant was used. Mouse n was not immunized (control). Mice were bleed and blood collected for antibody titer determinations (FIG. 3). Mice were given one more booster (30 ug) and then sacrificed and the spleen collected for hybridom development. The hybridom preparation method used was according to standard procedure (Harlow 1988).

Example 3

Screening for wtAβ1-42 Protofibril Specific Antibodies

An ELISA method was developed where by hybridom supernatants were screened for antibodies that bind Aβ1-42 protofibrils. Hybridom supernatant #258 showed high protofibril specificity (FIG. 3). The hybridom #258 was reseeded and screened again to ascertain a homogenous cell line. The monoclonal antibody that was produced from the #258 hybridom was defined as monoclonal antibody 258 (mAb258). Alternatively, screening (binding to Aβ protofibrils but not to Aβ monomers or fibrils) can be performed against an antibody phage display library, where the library has been made from RNA isolated from animals immunized with protofibril.

Example 4

Characterization of mAb 258 by Western Blot Analysis

The aim of the experiment was to determine if mAb 258 cross-reacts with wild type human amyloid precursor protein (wtAPP) or mutated human APP, APPswe, APP swe-arc (Nilsberth 2001, Mullan 1992) all of which contains uncleaved Aβ1-42. Cells were transfected with plasmids expressing human wtAPP, APPswe and APPswe-arc. Cells were subsequently harvested and solubilized and cellular proteins separated by SDS-PAGE and transferred to nitrocellulose filter papers and subsequently incubated with either mAb 258 or mAb 6E10. Specific binding of these antibodies to separated cellular proteins was detected by incubating the filter papers in a secondary anti-mouse IgG/IgM antibody solution and subsequent developed by incubation with Pierce super signal (art nr 34080-P) and a light sensitive film.

mAb 258 showed no binding to wtAPP, APPswe or APPswe-arc nor to wtAβ40 monomer, The commercial mAb 6E10 bound all these forms.

Example 5

Sandwich ELISA for Protofibril Characterization and Determinations

The specificity of mAb 258 was determined by a sandwich-ELISA. An 96-well ELISA plate was coated with mAb 258 over night at +4° C. After coating, wells were blocked with BSA for 1 hour at room temp. Aβ samples i.e wtAβ40 monomers, wtAβ42 protofibrils, wtAβ42-Arc protofibrils wtAβ42 fibrils, were added to the microtiterplate in 5× dilutions starting with 10 ug/ml. Samples were incubated for 1 hour at +4° C., after which 10 ng/well of a commercial secondary antibody, 6E10 (Signet) was added and incubated for 1 hour at room temp. Detection was achieved by incubation with a commercial ALP-conjugated anti-IgG antibody for 1 hour at room temp. and subsequent incubation with the substrate at room temp. for one hour according to the manufacturer's procedure. Samples were read in a microtiterplate reader (Spectra max 190 Molecular Devices, Sunyvale, USA) at 405 nm and 492 nm. FIG. 4A.

mAb 258 showed little or no cross-reactivity towards wtAβ40 monomers or wtAβ42 fibrils. Concentrations of wtAβ42 protofibrils down to 10 ng/ml were measurable.

Binding of an anti-Aβ42arc protofibril specific antibody (7E4) (Aβ42arc in protofibril conformation was used as a antigen during immunization) was measured in the sandwich-ELISA coated with increasing concentrations of wtAβ42 protofibrils. Detection was achieved by either an Aβ-specific mAb (1C3) as a secondary detection antibody (FIG. 4B) or by the commercial mAb 6E10, as secondary antibody (FIG. 4C). Strong binding of mAb 7E4 was achieved to wtAβ42 protofibrils. Concentration levels as low as 2-5 ng/ml of wtAβ42 protofibrils were measurable. The monoclonal antibodies 4E11 and 10F7 show less strong binding to wtAβ42 protofibrils (FIGS. 4B and 4C).

REFERENCES

Axelman K., et. al., Neurol., 51, 1193-1197, 1994
Bard F. et. al., Nature medicine, 6, 916-919, 2000
Cai, X-D. et. al., Science, 259, 514-516, 1993
Citron, M. et. al., Nature, 360, 672-674, 1992
DeMarco et. al., Proc. Natl. Acad. Sci., 101, 2293-2298, 2004
Dodard J-C. et. al. Nature medicine, 5 452-457, 2002
Glenner et. al., Biochem. Biophys. Res. Commun. 120, 885-890, 1984
Hardy, J. et. al., Nature Genet., 1, 233-234, 1992
Hartley D. M. et. al., J. Neuroscience 19, 8876-8884, 1999
Harlow E. et. al., Antibodies: A Laboratory Manual (Cold Spring Harbor) Lab. Press, Plainview, N.Y., 1988
Hoshi M. et. al., Proc. Natl. Acad. Sci., 100, 6370-6375, 2003
Janus C. V. et. al., Nature, 408, 979-982, 2000
Johnston, J. et. al., FEBS Lett., 354, 274-278, 1994
Kayed R. et. al., Science 300, 486-489, 2003
Klyubin et al., J. Physiol 551P, C32, commun., 2003
Lambert M. P. et. al., Proc. Natl. Acad. Sci., 95, 6448-6453, 1998
Lambert M. P. et. al., J. Neurochemistry, 79, 595-605, 2001
Lannfelt, L., et. al., Neurosci. Lett., 168, 254-256, 1994
Lannfelt L. et. al., Neurosci Lett., 199, 203-206, 1995
Masters et. al., Proc. Natl. Acad. Sci., 82, 4245-4249, 1985
McKhann, G., et. al., Neurology, 34, 939-944, 1984
Morgan D. et. al., Nature, 408, 982-985, 2000
Motter R. Et. al., Ann. Neurol., 38, 643-648, 1995
Mullan M. et. al., Nature Genet. 1, 345-347, 1992
Nicoll J. A. R. et. al., Nature medicine, 1-5, on line publ. 17 mars, 2003
Nilsberth C. et. al., Nat. Neurosci. 4, 887-893, 2001
Nilsson L. et. al., Swedish patent application 0400707-6, 2004
O'Nuallain B. et. al., PNAS 99, 1485-1490, 2002
Pirttilä et. al., J. Neurol. Sci., 127, 90-95, 1994
Scheuner D. et. al., Nature Med., 2, 864-869, 1996
Selkoe D. J., Ann. Rev. Cell Biol. 10, 373-403, 1994
Selkoe D. J., Annu. Rev. Neurosci. 17, 489-517, 1994
Seubert P. et. al., Nature, 359, 325-327, 1992
Sigurdsen E. M. et. al., Am. J. Pathol., 105, 439-447, 2001
Sthilerman M. et. al., Biochemistry 41, 3855-3860, 2002
Stine et. al., J. Protein Chem. 15, 193-203, 1996
Walsh D. M. et. al., J. Biol. Chem. 274, 25945-25952, 1999
Walsh D. M. et. al., Nature 416, 535-539, 2001
Weiner H. L. et. al., Ann. Neurol. 48, 567-579, 2000

The invention claimed is:

1. An isolated monoclonal antibody or antigen-binding fragment thereof that binds wild-type Aβ42/40 protofibril and Aβ42/40arc protofibril, and has no or little cross-reactivity to Aβ42/40 monomers.

2. The antibody of claim 1, wherein said antibody is an antigen-binding fragment.

3. The antibody of claim 1, wherein said antibody is humanized.

4. The antibody of claim 1, wherein said antibody is produced by immunizing and screening with at least >95% pure Aβ42/40arc protofibrils.

5. The antibody of claim 1, wherein said antibody is produced by immunizing and screening with at least >95% pure Aβ42/40 protofibrils.

6. The antibody of claim 1, wherein said antibody is a protofibril conformation specific antibody or antibody fragment.

7. A composition comprising one or more antibodies according to any of claims 1-2, 3, and 4-6.

8. A method of treating Alzheimer's disease comprising the step of administering to a patient having or suspected of having Alzheimer's disease, the antibody according to claim 1.

9. A method of treating Alzheimer's disease comprising the step of administering to a patient having or suspected of having Alzheimer's disease a composition comprising one or more antibodies according to any of claims 1-2, 3, and 4-6.

* * * * *

UNITED STATES PATENT AND TRADEMARK OFFICE
CERTIFICATE OF CORRECTION

PATENT NO. : 8,106,164 B2  
APPLICATION NO. : 11/570995  
DATED : January 31, 2012  
INVENTOR(S) : Pär Gellerfors et al.

Page 1 of 1

It is certified that error appears in the above-identified patent and that said Letters Patent is hereby corrected as shown below:

Page 3, under OTHER PUBLICATIONS, in Caughey and Lansbury, replace "Fibils," with --Fibrils,--.

Column 1, Lines 30-31, replace "argyrophillic proteineous" with --argyrophilic proteinaceous--.

Column 2, Line 31, replace "curvelinear" with --curvllinear--

Column 4, Line 67, replace "treatment that reduce" with --treatment that reduces--.

Column 5, Lines 50-51, replace "latter problems has been" with --latter problem has been--.

Column 13, Line 31, replace "monomer, The" with --monomer. The--;

Lines 42-43, replace "i.e wtAβ40 monomers" with -- i.e. wtAβ40 monomers--;

Line 53, replace "Sunyvale" with --Sunnyvale--.

Column 16, Claim 8, Line 23, replace "disease, the" with --disease the--.

Signed and Sealed this
Twelfth Day of February, 2013

Teresa Stanek Rea
*Acting Director of the United States Patent and Trademark Office*